(12) United States Patent
Winslow et al.

(10) Patent No.: US 7,205,398 B2
(45) Date of Patent: Apr. 17, 2007

(54) ETA-1 GENE AND METHODS FOR USE

(75) Inventors: Barbara J. Winslow, Del Mar, CA (US); Dalia Kalabat, El Cajon, CA (US)

(73) Assignee: Schering-Plough Animal Health Corporation, Union, NJ (US)

( * ) Notice: Subject to any disclaimer, the term of this patent is extended or adjusted under 35 U.S.C. 154(b) by 538 days.

(21) Appl. No.: 10/443,910

(22) Filed: May 22, 2003

(65) Prior Publication Data

US 2004/0022797 A1 Feb. 5, 2004

Related U.S. Application Data

(60) Provisional application No. 60/383,211, filed on May 24, 2002.

(51) Int. Cl.
*C07H 21/04* (2006.01)
*C12N 15/63* (2006.01)
*C12N 15/09* (2006.01)

(52) U.S. Cl. .................. 536/23.5; 435/69.1; 435/69.7; 435/235.1; 435/325; 435/320.1; 435/170; 435/252.3; 435/455; 530/350

(58) Field of Classification Search ............ None
See application file for complete search history.

(56) References Cited

U.S. PATENT DOCUMENTS

| | | |
|---|---|---|
| 5,047,237 A | 9/1991 | Cochran |
| 5,240,703 A | 8/1993 | Cochran |
| 5,382,425 A | 1/1995 | Cochran et al. |
| 5,506,128 A | 4/1996 | Cochran et al. |
| 5,593,873 A | 1/1997 | Cochran et al. |
| 5,763,269 A | 6/1998 | Cochran et al. |
| 5,925,358 A | 7/1999 | Cochran et al. |
| 5,965,138 A | 10/1999 | Cochran et al. |
| 6,001,369 A | 12/1999 | Cochran et al. |
| 6,033,904 A | 3/2000 | Cochran et al. |
| 6,121,043 A | 9/2000 | Cochran et al. |
| 6,127,163 A | 10/2000 | Cochran et al. |
| 6,136,318 A | 10/2000 | Cochran et al. |

FOREIGN PATENT DOCUMENTS

| | | |
|---|---|---|
| WO | WO 90/14092 | 11/1990 |
| WO | WO 91/06666 | 5/1991 |
| WO | WO 91/09955 | 7/1991 |
| WO | WO 94/03628 | 2/1994 |
| WO | WO 95/08622 | 3/1995 |
| WO | WO 98/50069 | 11/1998 |
| WO | WO 00/03030 | 1/2000 |
| WO | WO 00/61736 | 10/2000 |
| WO | WO 00/61773 | 10/2000 |

OTHER PUBLICATIONS

Oldberg, et al. PNAS 83:8819-8823, 1986 'Cloning and sequence analysis of rat bone sialoprotein (osteopontin) cDNA reveals an Arg-Gly-Asp cell binding sequence'.*
Hijiya, et al. Biochem. J. 303: 255-262, 1994 'Cloning and charcterization of the human osteopontin gene and its promoter'.*
MacEwen, EG, Biologics for Cancer Diagnosis, Prevention and Immunotherapy Meeting, Ames, IA, Apr. 12-13, 2001.
Senger, et al, "Transformed Mammalian Cells Secrete Specific Proteins and Phosphoproteins" *Cell* 16:885-893 (1979).
Cole, et al., "The EBV-Hybridoma Technique and Its Application to Human Lung Cancer" *Monoclonal Antibodies and Cancer Therapy* pp. 77-96 (1985).
Ulmer, et al., "Heterologous Protection Against Influenza by Injection of DNA Encoding a Viral Protein" *Science* 259:1745-1749 (1993).
Weber, et al., "Interaction Between CD44 and Osteopontin as a Potential Basis for Metastasis Formation" *Proceedings of Association of American Physicians* 109:1-9 (1997).
Biragyn, et al., "Genetic Fusion of Chemokines to a Self Tumor Antigen Induces Protective, T-cell Dependent Antitumor Immunity" *Nature Biotechnology* 17:253-258 (1999).
Gheradi, et al., "IL-12 delivery from Recombinant Vaccinia Virus Attenuates the Vector and Enhances the Cellular Immune Response Against HIV-1 Env in a Dose-Dependent Manner" *The Journal of Immunology* 162: 6724-6733 (1999).
Vail, et al., "Spontaneously Occuring Tumors of Companion Animals as Models for Human Cancer" *Cancer Investigation* 18:781-792 (2000).
Narvaiza, et al., "Intratumoral Coinjection of Two Adenoviruses, One Encoding the Chemokine IFN- γ-Inducible Protein-10 and Another Encoding IL-12, Results in Marked Antitumoral Synergy" *Journal of Immunology* 164:3112-3122 (2000).
Wu, et al., "Osteopontin is Required for Full Expression of the Transformed Phenotype by the *Ras* Oncogene" *British Journal of Cancer* 83:156-163 (2000).
Ashkar, et al., "Eta-1 (Osteopontin): An Entry Component of Type-1 (Cell-Mediated) Immunity" *Science* 287:860-864 (2000).
Kent, et al., "A recombinant avipoxvirus HIV-1 vaccine expressing interferon-gamma is safe and immunogenic in macaques" *Vaccine* 18:2250-2256 (2000).

* cited by examiner

*Primary Examiner*—Gary B Nickol
*Assistant Examiner*—Nirmal S. Basi

(57) ABSTRACT

The present application relates to osteopontin (Eta-1) polypeptides, nucleic acids that encode Eta-1, antibodies that specifically bind to Eta-1, and methods for enhancing an immune response in an animal.

20 Claims, 6 Drawing Sheets

Figure 1(A): Feline Eta-1 DNA Sequence (SEQ ID NO: 1)

a = adenine    g = guanine    c = cytosine    t = thymine
n = either adenine, guanine, cytosine or thymine
start and stop codons are underlined <u>atg</u>agantggcagtgatttgcttttgcctcttgggcattgcctacgccattccaattaaacagactgattctgggagctcggaggaa
aagcagctttacaacaaatacccagttgctgtagctacatggccaaagcctgacccatctcagaagcagactttcctagcactac
agaatgctgtgctctctgaagaaactgatgacttcaaacaaaagacccttgcaagtaagtccaatgaaagccatgatgtggatga
tgaagatgatgaagatgatgtagatagccaggactccgttgattcccatgacacagatgacnactctaaccagtctgatgaatct
gatgaactggtcactgactttcccaccgatgttccagcaacccaattttcaccccagctgtccccacaagagactcatatgatgg
ccgaggtgatagtgtggcttatggactgaggtccaaatctaagaagtcccacagatatgaagaccagtatcctgattctacagag
gaggacttcacatcacttgtgaaaagtcagagtatggaagatgacttcaatgccgtcctcctttcccacaccgtgcggcggtctcc
tgacagggacagccatgtgaaggacagtcaggaaacgagtcaggtggatgaccacagtatggaaccaagagccgcaagc
actccaaagagtataagctgaaggcaagtgatgagaacaataagcattcccatgagattggtagtcaggaaagttctgangtca
gcagtgagcttgttggccaaacagttcaaagcaatgaaaaggagcttagtccaacaccctgagagtgaggaacaagataaaca
cctgaaatttcgcgtttctcatgaattagatagttcatcttctgaggtcaat<u>taa</u>

Figure 1(B): Feline Eta-1 Amino Acid Sequence (SEQ ID NO: 2)

X = any amino acid

MRXAVICFCLLGIAYAIPIKQTDSGSSEEKQLYNKYPVAVATWPKPDPSQKQTFL
ALQNAVLSEETDDFKQKTLASKSNESHDVDDEDDEDDVDSQDSVDSHDTDDXS
NQSDESDELVTDFPTDVPATQFFTPAVPTRDSYDGRGDSVAYGLRSKSKKSHRY
EDQYPDSTEEDFTSLVKSQSMEDDFNAVLLSHTVRRSPDRDSHVKDSQETSQVD
DHSMEXKSRKHSKEYKLKASDENNKHSHEIGSQESSXVSSELVGQTVQSNEKEL
VQHPESEEQDKHLKFRVSHELDSSSSEVN

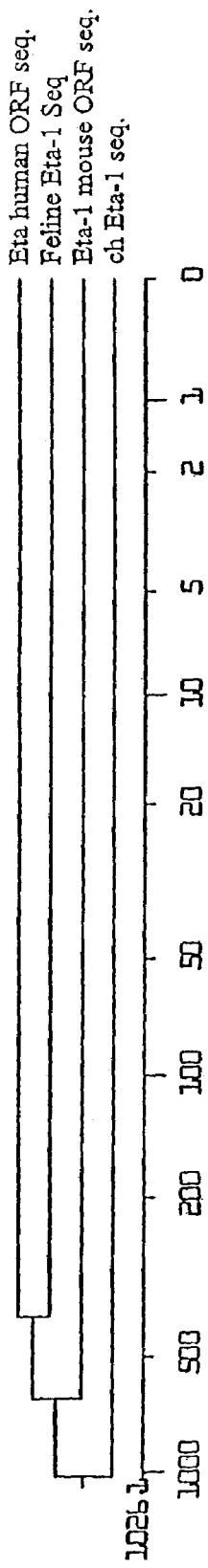
Figure 2(A): Phylogenetic Tree - Based on DNA Sequence
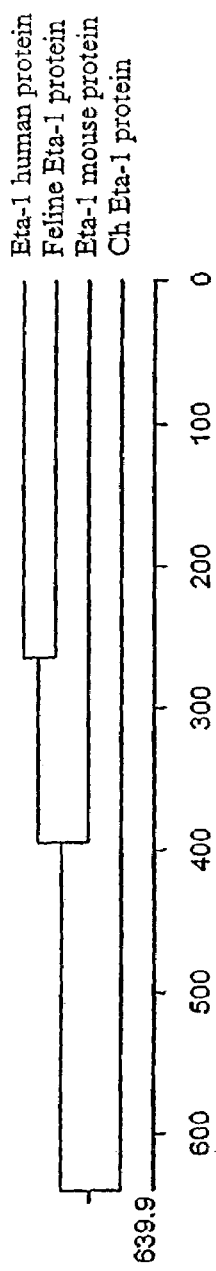
Figure 2(B): Phylogenetic Tree - Based on Amino Acid Sequence Figure 3: Protein Analysis
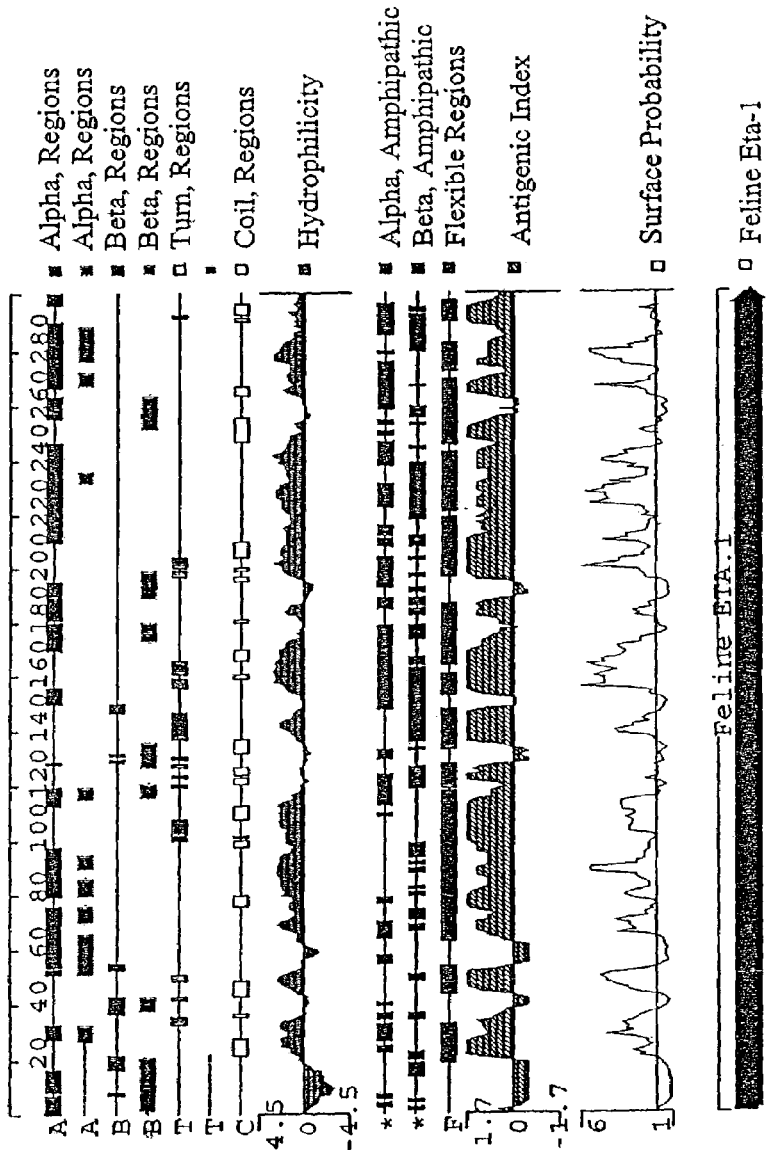

Figure 4(A): Canine Eta-1 Partial DNA Sequence (SEQ ID NO: 3)

a = adenine   g = guanine   c = cytosine   t = thymine   y = pyrimidine (t/u or c)

gcagaattcgcccttaagagatctcctagcgccacagaatgctgtgctgactgaggaaactgatgacttcaaacaaaaaccttc
tcaagtaagtccaatgaaagccatgacgatgtagatgaagatgatggagacgatgtggatagccaggactccgttgactcgaat
gacttagatgacgactccaacgagtctgatgaatccgatgaactggtcactgattttcccactgacattccagcaacccaattatc
actccagctgtccccacaagaggctcataygatggccgaggtgatagygtggtttatggatgtc

Figure 4(B): Canine Eta-1 Partial Amino Acid Sequence (SEQ ID NO: 4)

underline = N-glycosylation Sites and RGD

QNSPLRDLLAPQNAVLTEETDDFKQKTFSSKS<u>NES</u>HDDVDEDDGDDVDSQDSV
DSNDLDDDS<u>NES</u>DESDELVTDFPTDIPATQLFTPAVPTRGSYDG<u>RGD</u>SVVYGC

Figure 4(D): Sequence Homology with other Species - 320 bp Fragment

| Animal Source | Eta-1 DNA | Eta-1 Amino Acid |
|---|---|---|
| Feline | 88.5 | 85.9 |
| Human | 82.9 | 63.4 |
| Mouse | 64.1 | 54.3 |

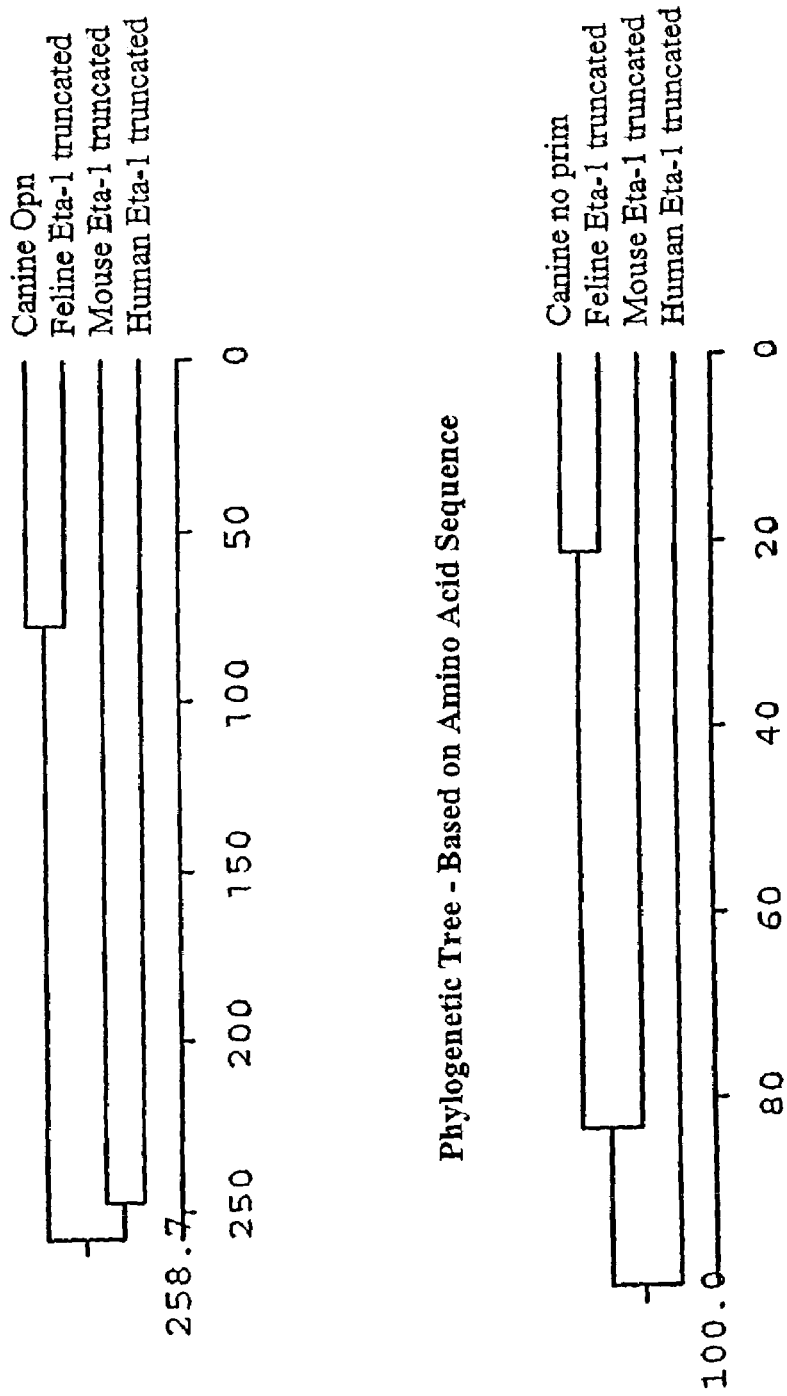

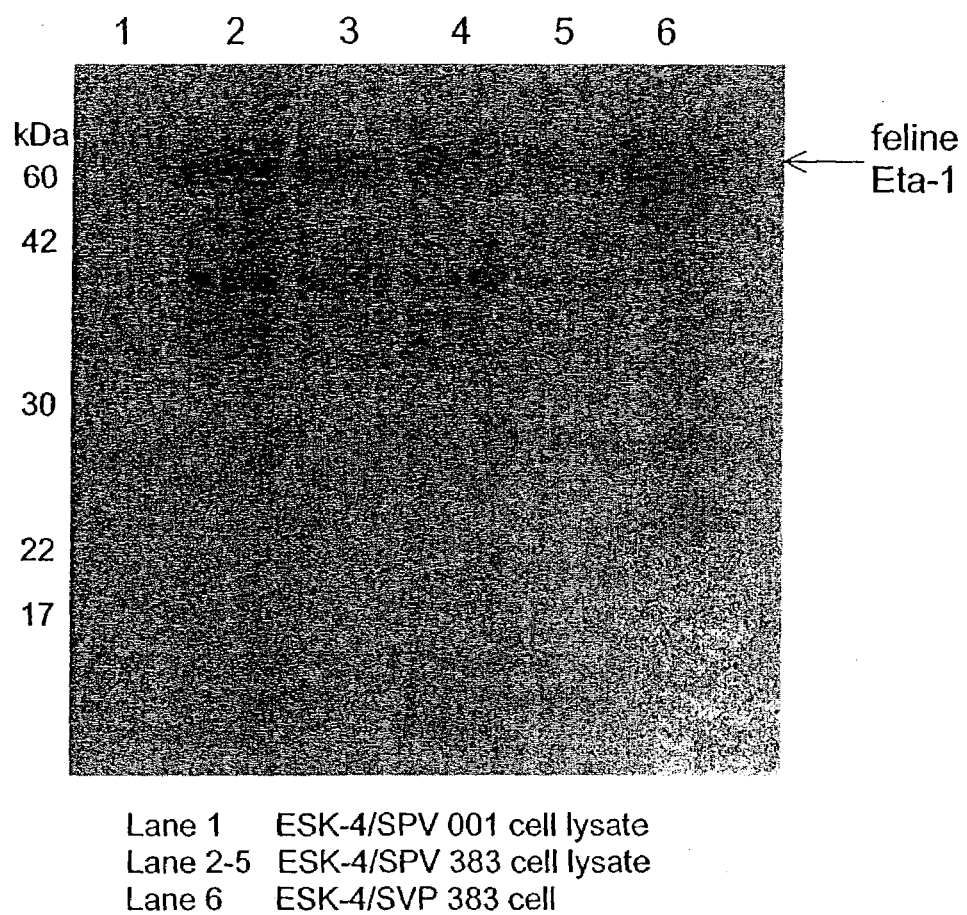
Figure 5: Western Blot
Lane 1    ESK-4/SPV 001 cell lysate
Lane 2-5  ESK-4/SPV 383 cell lysate
Lane 6    ESK-4/SVP 383 cell

SEQUENCE LISTING

<160> NUMBER OF SEQ ID NOS: 10

<210> SEQ ID NO 1
<211> LENGTH: 901
<212> TYPE: DNA
<213> ORGANISM: Artificial Sequence
<220> FEATURE:
<223> OTHER INFORMATION: Feline Eta-1 DNA Sequence
<220> FEATURE:
<221> NAME/KEY: misc_feature
<222> LOCATION: (7)..(7)
<223> OTHER INFORMATION: n = adenine, guanine, cytosine or thymine
<220> FEATURE:
<221> NAME/KEY: misc_feature
<222> LOCATION: (319)..(319)
<223> OTHER INFORMATION: n = adenine, guanine, cytosine or thymine
<220> FEATURE:
<221> NAME/KEY: misc_feature
<222> LOCATION: (664)..(664)
<223> OTHER INFORMATION: n = adenine, guanine, cytosine or thymine
<220> FEATURE:
<221> NAME/KEY: misc_feature
<222> LOCATION: (759)..(759)
<223> OTHER INFORMATION: n = adenine, guanine, cytosine or thymine

<400> SEQUENCE: 1
atgagantgg cagtgatttg cttttgcctc ttgggcattg cctacgccat tccaattaaa      60
cagactgatt ctgggagctc ggaggaaaag cagctttaca acaaataccc agttgctgta     120
gctacatggc caaagcctga cccatctcag aagcagactt tcctagcact acagaatgct     180
gtgctctctg aagaaactga tgacttcaaa caaaagaccc ttgcaagtaa gtccaatgaa     240
agccatgatg tggatgatga agatgatgaa gatgatgtag atagccagga ctccgttgat     300
tcccatgaca cagatgacna ctctaaccag tctgatgaat ctgatgaact ggtcactgac     360
tttcccaccg atgttccagc aacccaattt ttcaccccag ctgtccccac aagagactca     420
tatgatggcc gaggtgatag tgtggcttat ggactgaggt ccaaatctaa gaagtcccac     480
agatatgaag accagtatcc tgattctaca gaggaggact tcacatcact tgtgaaaagt     540
cagagtatgg aagatgactt caatgccgtc ctcctttccc acaccgtgcg gcggtctcct     600
gacagggaca gccatgtgaa ggacagtcag gaaacgagtc aggtggatga ccacagtatg     660
gaanccaaga gccgcaagca ctccaaagag tataagctga aggcaagtga tgagaacaat     720
aagcattccc atgagattgg tagtcaggaa agttctgang tcagcagtga gcttgttggc     780
caaacagttc aaagcaatga aaaggagctt agtccaacac cctgagagtg aggaacaaga     840
taaacacctg aaatttcgcg tttctcatga attagatagt tcatcttctg aggtcaatta     900
a                                                                     901

<210> SEQ ID NO 2
<211> LENGTH: 299
<212> TYPE: PRT
<213> ORGANISM: Artificial Sequence
<220> FEATURE:
<223> OTHER INFORMATION: Feline Eta-1 Amino Acid Sequence
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (107)..(107)
<223> OTHER INFORMATION: Xaa = any amino acid
<220> FEATURE:
<221> NAME/KEY: MISC_FEATURE
<222> LOCATION: (222)..(222)
<223> OTHER INFORMATION: Xaa = any amino acid
<220> FEATURE:
<221> NAME/KEY: MISC_FEATURE
<222> LOCATION: (253)..(253)

<223> OTHER INFORMATION: Xaa = any amino acid

<400> SEQUENCE: 2

```
Met Arg Xaa Ala Val Ile Cys Phe Cys Leu Leu Gly Ile Ala Tyr Ala
1               5                   10                  15

Ile Pro Ile Lys Gln Thr Asp Ser Gly Ser Ser Glu Lys Gln Leu
            20                  25                  30

Tyr Asn Lys Tyr Pro Val Ala Val Ala Thr Trp Pro Lys Pro Asp Pro
        35                  40                  45

Ser Gln Lys Gln Thr Phe Leu Ala Leu Gln Asn Ala Val Leu Ser Glu
    50                  55                  60

Glu Thr Asp Asp Phe Lys Gln Lys Thr Leu Ala Ser Lys Ser Asn Glu
65                  70                  75                  80

Ser His Asp Val Asp Asp Glu Asp Asp Asp Val Asp Ser Gln
                85                  90                  95

Asp Ser Val Asp Ser His Asp Thr Asp Asp Xaa Ser Asn Gln Ser Asp
                100                 105                 110

Glu Ser Asp Glu Leu Val Thr Asp Phe Pro Thr Asp Val Pro Ala Thr
            115                 120                 125

Gln Phe Phe Thr Pro Ala Val Pro Thr Arg Asp Ser Tyr Asp Gly Arg
    130                 135                 140

Gly Asp Ser Val Ala Tyr Gly Leu Arg Ser Lys Ser Lys Ser His
145                 150                 155                 160

Arg Tyr Glu Asp Gln Tyr Pro Asp Ser Thr Glu Glu Asp Phe Thr Ser
                165                 170                 175

Leu Val Lys Ser Gln Ser Met Glu Asp Asp Phe Asn Ala Val Leu Leu
            180                 185                 190

Ser His Thr Val Arg Arg Ser Pro Asp Arg Asp Ser His Val Lys Asp
        195                 200                 205

Ser Gln Glu Thr Ser Gln Val Asp Asp His Ser Met Glu Xaa Lys Ser
    210                 215                 220

Arg Lys His Ser Lys Glu Tyr Lys Leu Lys Ala Ser Asp Glu Asn Asn
225                 230                 235                 240

Lys His Ser His Glu Ile Gly Ser Gln Glu Ser Ser Xaa Val Ser Ser
                245                 250                 255

Glu Leu Val Gly Gln Thr Val Gln Ser Asn Glu Lys Glu Leu Val Gln
            260                 265                 270

His Pro Glu Ser Glu Glu Gln Asp Lys His Leu Lys Phe Arg Val Ser
        275                 280                 285

His Glu Leu Asp Ser Ser Ser Ser Glu Val Asn
    290                 295
```

<210> SEQ ID NO 3
<211> LENGTH: 320
<212> TYPE: DNA
<213> ORGANISM: Artificial Sequence
<220> FEATURE:
<223> OTHER INFORMATION: Canine Eta-1 DNA Sequence (partial gene)

<400> SEQUENCE: 3

```
gcagaattcg cccttaagag atctcctagc gccacagaat gctgtgctga ctgaggaaac    60
tgatgacttc aaacaaaaaa ccttctcaag taagtccaat gaaagccatg acgatgtaga   120
tgaagatgat ggagacgatg tggatagcca ggactccgtt gactcgaatg acttagatga   180
cgactccaac gagtctgatg aatccgatga actggtcact gattttccca ctgacattcc   240
```

```
agcaacccaa ttattcactc cagctgtccc cacaagaggc tcataygatg gccgaggtga      300
tagygtggtt tatggatgtc                                                  320
```

<210> SEQ ID NO 4
<211> LENGTH: 106
<212> TYPE: PRT
<213> ORGANISM: Artificial Sequence
<220> FEATURE:
<223> OTHER INFORMATION: Canine Eta-1 Amino Acid Sequence (partial ORF)

<400> SEQUENCE: 4

```
Gln Asn Ser Pro Leu Arg Asp Leu Leu Ala Pro Gln Asn Ala Val Leu
1               5                   10                  15

Thr Glu Glu Thr Asp Asp Phe Lys Gln Lys Thr Phe Ser Ser Lys Ser
            20                  25                  30

Asn Glu Ser His Asp Asp Val Asp Glu Asp Asp Gly Asp Asp Val Asp
        35                  40                  45

Ser Gln Asp Ser Val Asp Ser Asn Asp Leu Asp Asp Ser Asn Glu
    50                  55                  60

Ser Asp Glu Ser Asp Glu Leu Val Thr Asp Phe Pro Thr Asp Ile Pro
65              70                  75                  80

Ala Thr Gln Leu Phe Thr Pro Ala Val Pro Thr Arg Gly Ser Tyr Asp
                85                  90                  95

Gly Arg Gly Asp Ser Val Val Tyr Gly Cys
            100                 105
```

<210> SEQ ID NO 5
<211> LENGTH: 32
<212> TYPE: DNA
<213> ORGANISM: Artificial Sequence
<220> FEATURE:
<223> OTHER INFORMATION: Feline Eta-1 sense primer

<400> SEQUENCE: 5

```
accatgagat tggcagtgat ttgcttttgc ct                                    32
```

<210> SEQ ID NO 6
<211> LENGTH: 38
<212> TYPE: DNA
<213> ORGANISM: Artificial Sequence
<220> FEATURE:
<223> OTHER INFORMATION: Feline Eta-1 antisense primer

<400> SEQUENCE: 6

```
ttaattgacc tcagaagatg cactatctaa ttcatgag                              38
```

<210> SEQ ID NO 7
<211> LENGTH: 25
<212> TYPE: DNA
<213> ORGANISM: Artificial Sequence
<220> FEATURE:
<223> OTHER INFORMATION: Feline Eta-1 sense primer

<400> SEQUENCE: 7

```
gactgaattc atgagattgg cagtg                                            25
```

<210> SEQ ID NO 8
<211> LENGTH: 24
<212> TYPE: DNA
<213> ORGANISM: Artificial Sequence
<220> FEATURE:
<223> OTHER INFORMATION: Feline Eta-1 antisense primer -continued

```
<400> SEQUENCE: 8
ggtaggatcc ttaattgacc tcag                                              24

<210> SEQ ID NO 9
<211> LENGTH: 39
<212> TYPE: DNA
<213> ORGANISM: Artificial Sequence
<220> FEATURE:
<223> OTHER INFORMATION: Canine Eta-1 sense primer
<220> FEATURE:
<221> NAME/KEY: misc_feature
<222> LOCATION: (30)..(30)
<223> OTHER INFORMATION: w = adenine or thymine/uracil
<220> FEATURE:
<221> NAME/KEY: misc_feature
<222> LOCATION: (33)..(33)
<223> OTHER INFORMATION: s = guanine or cytosine

<400> SEQUENCE: 9
cctgacccat ctcagaagca gaatctcctw gcsccacag                              39

<210> SEQ ID NO 10
<211> LENGTH: 35
<212> TYPE: DNA
<213> ORGANISM: Artificial Sequence
<220> FEATURE:
<223> OTHER INFORMATION: Canine Eta-1 antisense primer
<220> FEATURE:
<221> NAME/KEY: misc_feature
<222> LOCATION: (16)..(16)
<223> OTHER INFORMATION: r = guanine or adenine
<220> FEATURE:
<221> NAME/KEY: misc_feature
<222> LOCATION: (20)..(20)
<223> OTHER INFORMATION: m = adenine or cytosine
<220> FEATURE:
<221> NAME/KEY: misc_feature
<222> LOCATION: (21)..(21)
<223> OTHER INFORMATION: r = guanine or adenine

<400> SEQUENCE: 10
gacctcagtc cataarccam rctatcacct cggcc                                  35
```

ETA-1 GENE AND METHODS FOR USE

This application claims priority under 35 U.S.C. § 119(e) to U.S. Provisional Application Ser. No. 60/383,211, filed May 24, 2002, which is incorporated herein by reference in its entirety.

FIELD OF THE INVENTION

The present invention relates to a novel cytokine, referred to as osteopontin (Eta-1), to nucleic acids that encode Eta-1 and to antibodies that specifically recognize and bind to Eta-1. More particularly, the invention relates to feline and canine Eta-1 and its use in compositions for the prevention or treatment of infectious diseases or cancer.

BACKGROUND OF THE INVENTION

Currently there are no successful vaccines for the prevention of feline immunodeficiency disease (FIV) and feline infectious peritonitis (FIP) disease in cats. Current feline leukemia virus (FeLV) vaccines are available, but their level of efficacy remains questionable and, in some cases, may cause the disease. Therefore, there is a need in the art for agents and compositions that provide protection from these and other diseases where there is not yet an existing vaccine or that improve the efficacy of existing and commonly used vaccines. In addition, vaccination of kittens is difficult due to the inability to overcome maternal antibodies in the kittens. Safe and effective agents to help overcome these barriers are also needed. Protection against FIV, FeLV and FIP infection has been correlated with the induction of cytotoxic T cell responses. Anti-FIV and FeLV antibodies have also been shown to be important for successful clearance of these viruses. However, in some cases, anti-FIV envelope antibodies have been implicated in causing enhancement of disease. Anti-FIP spike (Env) antibodies have also been correlated with the induction of enhanced disease and early death after challenge of kittens immunized with vaccines containing FIP spike proteins. A dominant Th2 T cell response has also been observed in the progression of HIV disease. Therefore, vaccines or gene therapies, which induce a strong CTL response are needed.

Nearly one-half of the households in the U.S. have at least one companion animal. In the U.S. alone, there are 55 million dogs and 60 million cats. Cancer is the number one cause of death in dogs and number two cause of death in cats. In one large necropsy study, 23% of dogs died of cancer regardless of age and 43% died of cancer after 10 years of age. 26% of cats died of cancer. Dog and cat cancers are currently treated by resection/amputation, radiation and chemotherapy. Human chemotherapy drugs are used off-label. Combination therapy is common. However, in many cases, treatment regimes are highly toxic, often ineffective and palliative, at best. (Vail D M, MacEwen E G., Cancer Investigation, 18[8]: 781 (2000). MacEwen E G. Presentation given at Biologics for Cancer Diagnosis, Prevention and Immunotherapy Meeting, Ames, I A, Apr. 12–13, 2001.) Novel approaches involving the use of biological molecules, such as Eta-1, presented here, have potential for being non-toxic, effective alternatives to standard tumor therapies. There are no cancer treatments currently available, registered specifically for animal use.

Common cat cancers are lymphoma/leukemia, fibrosarcomas, mammary carcinoma, soft tissue sarcoma, and oral squamous cell cancers. Common dog cancers are melanoma, mast cell tumors, soft tissue sarcoma, oral cancers, squamous cell carcinoma, osteosarcoma, and non-hodgkins lymphomas.

Cytotoxic T lymphocytes are the primary effectors of an anti-cancer immune response, mediated by direct and indirect tumor cell killing, or through the release of cytokines capable of interfering with tumor cell growth. Antibodies have a minor role in the rejection of cancer cells. Tumor cells are classified as foreign antigens because they express tumor associated antigens not present in other adult tissues. Still, malignant cells are not recognized by the immune system. Biological agents that increase cytotoxic T cell responses and the production of Th1 cytokines are predicted to have significant potential for cancer treatment as well as for vaccination against cancer.

The Th1/Th2 paradigm predicts that early expression of Th1 cytokines (IFNγ, IL-12, IL-2, TNF) is critical in the generation of a protective immune response against intracellular pathogens, such as viruses and induction of cytotoxic T killer effector cells. Factors augmenting Th1 and inhibiting Th2 cytokine expression (IL-10, IL-4, IL-5) might function as powerful modulators of cell-mediated immunity. The development of cell-mediated (type-1) immune responses is necessary for protection against the growth of many infectious pathogens and can mediate autoimmune host tissue destruction. An essential early step in macrophage activation by microbial pathogens and foreign body reactions is macrophage production of IL-12 at sites of infection, whereas early IL-10 production inhibits this response. Although IL-12 responses can be triggered by an interaction between the CD40 ligand on activated T cells and CD40 on macrophages, this interaction also induces the inhibitory IL-10 cytokine, and its transient nature may not suffice for sustained IL-12 induction in vitro or in vivo.

A gene product that may play an important role in the development of type-1 immunity is the T cell cytokine Eta-1 (for early T lymphocyte activation-1), also known as osteopontin. Eta-1 mRNA is the most abundant early RNA transcript induced in Con-A activated murine T cells (Senger et al., 1979, Cell, 16: 885). Eta-1 is a 60 kDa secreted phosphoprotein containing an RGD domain. The RGD sequence contained in Eta-1 is an integrin-binding motif common to many extracellular matrix (ECM) proteins. The Eta-1 gene is expressed in T cells early in the course of bacterial infections (within 48 hours), and interaction of its protein product with macrophages can induce inflammatory responses. Genetic resistance to infection by certain strains of *Rickettsia* may depend on Eta-1-dependent attraction of monocytes into infectious sites and acquisition of bactericidal activity. Furthermore, the granulomatous responses characteristic of sarcoidosis and tuberculosis are associated with high levels of Eta-1 expression.

Eta-1 enhances Th1 and inhibits Th2 cytokine expression. It directly induces macrophages to induce the production of IL-12, and inhibits IL-10 production. Eta-1 also costimulates T cell proliferation. Eta-1 increases CD3-mediated T-cell production of interferon gamma and CD40 ligand, which augments T-cell dependent IL-12 production by human monocytes. Eta-1 can also induce proliferation of B-cells and antibody production through the involvement of CD40L of B cells. Eta-1 is chemoattractant and supports adhesion of human and murine T cells and macrophages in vitro. In vivo, macrophages accumulate at sites of subcutaneous injection of Eta-1. In addition, Eta-1 may directly induce chemotaxis and indirectly facilitate macrophage migration to other chemoattractants. In vitro migratory and adhesive effects of Eta-1 are mediated by RGD-dependent (integrin) and RGD-independent (CD44) receptors. Eta-1 deficient mice exhibit a five-fold reduction in macrophage infiltration compared with wild-type controls following renal injury. Further, subcutaneous injection of polyvinylpyrrolidone (PVP) induces macrophage-rich granulomas and cellular accumulation after PVP injection is markedly reduced in Eta-1 deficient mice.

Ashkar et al., "Eta-1 (Osteopontin): An Early Component of Type-1 (Cell-Mediated) Immunity", *Science*, 287: 860–64 (2000), found that mice deficient in Eta-1 gene expression have severely impaired type-1 immunity to viral infection and bacterial infection and do not develop sarcoid-type granulomas. Eta-1 deficient mice also exhibited diminished IL-12 and interferon-γ production and increased IL-10 production. Ashkar et al. also observed a phosphorylation dependent interaction between the amino-terminal portion of Eta-1 and its integrin receptor mediated stimulation of IL-12 expression and a phosphorylation independent interaction with CD44 mediated inhibition of IL-10 expression. Based on these observations, Ashkar et al. concluded that Eta-1 is a key cytokine that sets the stage for efficient type-1 immune responses through differential regulation of macrophage IL-12 and IL-10 expression.

Eta-1 has also been implicated in various other events that are important to cell-mediated immunity. For example, Eta-1 is associated with monocyte-macrophage differentiation, giant cell formation and the inhibition of apoptosis in various cell types, including pro-B cells. Eta-1 also inhibits nitric oxide production by macrophages and has been associated with tissue repair, fibrosis and dystrophic calcification after immunological injury.

These observations support the idea that Eta-1 polypeptides may be used to initiate or enhance an immune response to an immunogen (viral, bacterial or tumor) in an animal, e.g., by supporting adhesion of T cells and macrophages. Such molecules have use as adjuvants in immunogenic compositions, as well as, e.g., in treating animals suffering from a condition caused by inappropriate altered T cell or macrophage response.

While Eta-1 has been shown to have a recently identified pro-inflammatory role in Th1-mediated immunity, it also appears to have anti-inflammatory effects in different pathological responses. Eta-1 appears to have a role in aberrant tissue repair, has been associated with ras oncogenic transformation of cells (Wu et al. 2000, Brit. J. Cancer, 83: 156–163) and is involved in interactions with CD44 and the formation of metastasis (Weber et al., 1997. Proc. Assoc. Amer. Phys. 109: 1–9). Therefore, Eta appears to have heterogeneic function, and its precise roles in vivo are not completely understood. The multifunctional nature of Eta-1 may reflect the expression of specific isoforms, its secretion as a soluble protein, the location and timing of secretion, and the co-expression of other regulatory factors. Therefore, Eta-1, if appropriately administered, may have multiple applications for use in the treatment of disease (viral, bacterial or tumorigenic). In addition for use as a biological vaccine adjuvant to enhance cell mediated immunity and treatment of cancer, Eta-1 may have use in the treatment of autoimmune diseases, such as osteoarthritis, rheumatoid arthritis, diabetes, and skin diseases.

SUMMARY OF THE INVENTION

The present invention provides an isolated Eta-1 polypeptide derived from a species of an animal selected from the group consisting of cats and dogs.

The invention also provides nucleic acids encoding an Eta-1 polypeptide, such as that described above, as well as expression vectors containing the nucleic acids of the invention and host cells genetically modified to express the nucleic acid. Still further, the invention provides antibodies or fragments thereof that specifically bind to an Eta-1 polypeptide.

Moreover, the present invention provides compositions including immunogenic compositions and/or vaccines containing an immunogen and an Eta-1 polypeptide, as described above. Also provided are compositions, immunogenic compositions and/or vaccines containing nucleic acids encoding an immunogen, an Eta-1 polypeptide, and/or fusion proteins containing the immunogen and Eta-1 polypeptide, optionally including a pharmaceutically acceptable carrier, diluent, or excipient. The nucleic acids of the invention may also be administered in an expression vector, which may also contain a nucleic acid sequence of one or more immunogenic polypeptides.

The invention also provides a method for enhancing an immune response in an animal to an immunogen that includes administering to the animal an effective amount of the immunogen and an Eta-1 polypeptide described above. The method of the invention may include administering the immunogen, a nucleic acid encoding the immunogen, or an expression vector containing a nucleic acid encoding the immunogen, together with the Eta-1 polypeptide, a nucleic acid encoding the polypeptide, or an expression vector containing a nucleic acid encoding the polypeptide. The method of the present invention also contemplates administering a fusion polypeptide including (a) an amino acid sequence of an immunogenic polypeptide; and (b) an amino acid sequence of an Eta-1 polypeptide, as described above.

The immunogens used in the compositions and methods of the invention may be derived from a pathogen. Examples of such pathogens include viral, bacterial, rickettsial, protozoal, fungal, and parasitic pathogens (including trematodes (flukes), cestodes (tapeworms), nematodes (roundworms) and arthropods), or combinations thereof.

Eta-1 may also be mixed or presented in combination with tumor associated antigens, fixed tumor cells, immune cells (such as dendritic cells), or immune costimulatory receptors and ligands (such as B7.1, B17.2, CD40L, CTLA4 and CD28).

These and other alternative non-limiting embodiments of the present invention will described in the following description and in the attached figures.

BRIEF DESCRIPTION OF THE DRAWINGS

FIG. 1(A) shows the cDNA of feline Eta-1 ligand (SEQ ID NO: 1), and FIG. 1(B) shows the amino acid sequence of feline Eta-1 ligand (SEQ ID NO: 2).

FIG. 2(A) shows the phylogenetic tree of human, feline, mouse, and chicken Eta-1 based on the DNA sequence, and FIG. 2(B) shows the phylogenetic tree of human, feline, mouse, and chicken Eta-1 based on the amino acid sequence.

FIG. 3 shows a protein analysis of feline Eta-1 [WINDOWS 32 PROTEAN 4.05, DNA STAR, Inc.); Hydrophilicity: Kyte Doolittle; Antigenic: index: Jameson Wolt]

FIG. 4(A) shows the cDNA of canine Eta-1 ligand (SEQ ID NO:3) and FIG. 4(B) shows the amino acid sequence of canine Eta-1 (SEQ ID NO: 4). FIG. 4(C) shows the phylogenetic tree of canine Eta-1, and the sequence homology of Eta-1 from feline, human and mouse.

FIG. 5 is a Western Blot showing the expression of feline Eta-1 using goat anti-human Eta-1.

DETAILED DESCRIPTION OF THE INVENTION

The present invention relates, in a preferred embodiment, to peptides derived from a species of an animal selected from feline and canine. Preferably, the animal is a feline. Species of feline encompassed within the present invention include, without limitation, domesticated cat, tiger, lion, bobcat, cheetah, jaguar, leopard, and the like, and subspecies thereof. Species of canine encompassed within the present invention include domesticated dogs.

General Definitions

The terms used in this specification generally have their ordinary meanings in the art, within the context of this invention and in the specific context where each term is used. Numerical quantities given herein are approximate unless stated otherwise, meaning that the terms "about" or "approximately" can be inferred when not expressly stated. Certain terms are discussed below, or elsewhere in the specification, to provide additional guidance to the practitioner in describing the compositions and methods of the invention and how to make and use them.

As used herein, the term "isolated" means that the referenced material is removed from the environment in which it is found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. Isolated nucleic acid molecules include sequences inserted into plasmids, cosmids, artificial chromosomes, and the like. Thus, the term "isolated nucleic acid" includes a recombinant nucleic acid. An isolated protein may be associated with other proteins or nucleic acids, or both, with which it associates in the cell, or with cellular membranes if it is a membrane-associated protein. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell. Methods for purification are well-known in the art, and examples are discussed below. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

A purified material may contain less than about 50%, preferably less than about 75%, and most preferably less than about 90%, of the cellular components with which it was originally associated. The term "substantially pure" indicates the highest degree of purity, which can be achieved using conventional purification techniques known in the art.

A "sample" as used herein refers to a biological material which can be tested, e.g., for the presence of Eta-1 polypeptides or Eta-1 nucleic acids, e.g., to identify cells that specifically express the Eta-1 gene and its gene product. Such samples can be obtained from any source, including tissue, tumorigenic tissue; blood and blood cells, including circulating hematopoietic stem cells (for possible detection of protein or nucleic acids), plural effusions, cerebrospinal fluid (CSF), ascites fluid, and cell culture.

The term "molecule" means any distinct or distinguishable structural unit of matter comprising one or more atoms, and includes, for example, polypeptides and polynucleotides.

An "immunogenic composition" of the invention, as used herein, refers to any composition that elicits an immune response in an animal. An "immune response" is the reaction of the body to foreign substances, without implying a physiologic or pathologic consequence of such a reaction, i.e., without necessarily conferring protective immunity on the animal. An immune response may include one or more of the following: (a) a cell mediated immune response, which involves the production of lymphocytes by the thymus (T cells) in response to exposure to the antigen; and/or (b) a humoral immune response, which involves production of plasma lymphocytes (B cells) in response to antigen exposure with subsequent antibody production.

The term "vaccine", as used herein, broadly refers to any compositions that may be administered to an animal to protect the animal against an infectious disease. The term "protect", "protective immune response" or "protective immunity", as used herein to describe vaccines, means protection of the animal from challenge with a foreign substance. Vaccines protect against diseases by inducing or increasing an immune response in an animal against the infectious disease.

The term "effective amount" refers to an amount of a compound or compositions that is sufficient to provide a desired result. Thus, as used to describe a vaccine, an effective amount refers to an amount of a compound or composition (e.g., an antigen) that is sufficient to produce or elicit a protective immune response. An effective amount with respect to an immunological composition is an amount that is sufficient to elicit an immune response, whether or not the response is protective.

In accordance with the present invention, there may be employed conventional molecular biology, microbiology and recombinant DNA techniques within the skill of the art. Such techniques are explained fully in the literature. See, e.g., Sambrook, Fitsch & Maniatis, *Molecular Cloning: A Laboratory Manual*, Second Edition Cold Spring Harbor Laboratory Press, Cold Spring Harbor, N.Y. (1989) (referred to herein as "Sambrook et al., 1989").

The term "polynucleotide" or "nucleic acid" sequence as used herein refers to and means any chain of two or more nucleotides. Nucleotides are phosphate esters of pentoses in which a nitrogenous base is linked to C(1') of the sugar residue. Such bases are typically adenine, guanine, cytosine, uracil, thymine, and hypoxanthine, but some may be modified bases, for example, thio-uracil, thio-guanine and fluoro-uracil.

A nucleotide sequence frequently carries genetic information, including the information used by cellular machinery to make proteins and enzymes. The terms include genomic DNA, cDNA, RNA, any synthetic and genetically manipulated polynucleotides, and both sense and antisense polynucleotides. This includes single- and double-stranded molecules as well as backbone modifications thereof (for example, methylphosphonate linkages); i.e., DNA-DNA, DNA-RNA, and RNA-RNA hybrids as well as "protein nucleic acids" (PNA) formed by conjugating bases to an amino acid backbone.

The polynucleotides herein may be flanked by natural regulatory sequences, or may be associated with heterologous sequences, including promoters, enhancers, response elements, signal sequences, polyadenylation sequences, introns, 5'- and 3'-non-coding regions and the like. The nucleic acids may also be modified by many means known in the art. Non-limiting examples of such modifications include methylation, "caps", substitution of one or more of the naturally occurring nucleotides with an analog, and internucleotide modifications. Polynucleotides may contain one or more additional covalently linked moieties, such as proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.) and alkylators to name a few. The polynucleotides may be derivatized by formation of a methyl or ethyl phosphotriester or an alkyl phosphoramidite linkage. Furthermore, the polynucleotides herein may also be modified with a label capable of providing a detectable signal, either directly or indirectly. Exemplary labels include radioisotopes, fluorescent molecules, biotin and the like. Other non-limiting examples of modification which may be made are provided, below, in the description of the present invention.

A "polypeptide" is a chain of chemical building blocks called amino acids that are linked together by chemical bonds called "peptide bonds". The term "protein" refers to polypeptides that contain the amino acid residues encoded by a gene or by a nucleic acid molecule (e.g., an mRNA or a cDNA) transcribed from that gene either directly or indirectly. Optionally, a protein may lack certain amino acid residues that are encoded by a gene or by an mRNA. For example, a gene or mRNA molecule may encode a sequence of amino acid residues on the N-terminus of a protein (i.e., a signal sequence) that is cleaved from, and therefore may not be part of, the final protein. A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant.

A "ligand" is, broadly speaking, any molecule that binds to another molecule. In preferred embodiments, the ligand is either a soluble molecule or the smaller of the two molecules or both. The other molecule may be referred to as a "receptor". In preferred embodiments, both a ligand and its receptor are molecules (preferably proteins or polypeptides) produced by cells. Preferably, a ligand is a soluble molecule and the receptor is an integral membrane protein (i.e., a protein expressed on the surface of a cell). In a particularly preferred embodiment of the invention a ligand is an Eta-1 polypeptide and the receptor is an Eta-1 receptor that specifically recognizes Eta-1.

"Amplification" of a polynucleotide, as used herein, denotes the use of polymerase chain reaction (PCR) to increase the concentration of a particular DNA sequence within a mixture of DNA sequences. For a description of PCR see Saiki et al., *Science,* 239: 487 (1988).

"Chemical sequencing" of DNA denotes methods such of Maxam-Gilbert (see Maxam & Gilbert, *Proc. Natl. Acad. Sci. U.S.A.* (1977), 74: 560), in which DNA is cleaved using individual base-specific reactions.

"Enzymatic sequencing" of DNA denotes methods such as that of Sanger (Sanger et al., *Proc. Natl. Acad. Sci. U.S.A.* (1977), 74: 5463) and variations thereof well known in the art, in a single-stranded DNA is copied and randomly terminated using DNA polymerase.

A "gene" is a sequence of nucleotides which code for a functional "gene product". Generally, a gene product is a functional protein. However, a gene product can also be another type of molecule in a cell, such as an RNA (e.g., a tRNA or a rRNA). For the purposes of the present invention, a gene product also refers to an mRNA sequence which may be found in a cell. For example, measuring gene expression levels according to the invention may correspond to measuring mRNA levels. A gene may also comprise regulatory (i.e., non-coding) sequences as well as coding sequences. Exemplary regulatory sequences include promoter sequences, which determine, for example, the conditions under which the gene is expressed. The transcribed region of the gene may also include untranslated regions including introns, a 5'-untranslated region (5'-UTR) and a 3'-untranslated region (3'-UTR).

A "coding sequence" or a sequence "encoding" an expression product, such as a RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

An "expression control sequence" is a DNA regulatory region capable of facilitating the information in a gene or DNA sequence to become manifest, e.g., producing RNA (rRNA or mRNA) or a protein by activating the cellular functions involved in transcription and translation of a corresponding gene or DNA sequence. For example, an expression control sequence may include a promoter sequence, which is a DNA regulatory region capable of binding RNA polymerase in a cell and initiating transcription of a downstream (3' direction) coding sequence. The expression control sequence may also include an enhancer sequence which is a DNA sequence capable of increasing the transcription of a gene into mRNA. The constructs of the present invention may contain a promoter alone or in combination with an enhancer, and these elements need not be contiguous.

A coding sequence is "under the control of" or is "operatively associated with" transcriptional and translational control sequences in a cell when RNA polymerase transcribes the coding sequence into RNA, which is then trans-RNA spliced (if it contains introns) and, if the sequence encodes a protein, is translated into that protein.

The term "transfection" means the introduction of a foreign nucleic acid into a cell. The term "transformation" means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed". The DNA or RNA introduced to a host cell can come from any source, including cells of the same genus or species as the host cell or cells of a different genus or species.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are discussed in greater detail below.

The term "expression system" means a host cell and compatible vector under suitable conditions, e.g., for the expression of a protein coded for by foreign DNA carried by the vector and introduced to the host cell. Common expression systems include *E. coli* host cells and plasmid vectors, insect host cells such as Sf9, Hi5 or S2 cells and Baculovirus vectors, *Drosophila* cells (Schneider cells) and expression systems, and mammalian host cells and vectors.

The term "heterologous" refers to a combination of elements not naturally occurring. For example, heterologous DNA refers to DNA that is not naturally located in the cell, or in a chromosomal site of the cell. Preferably, heterologous DNA includes a gene foreign to the cell. A heterologous expression regulatory element is a regulatory element operatively associated with a different gene that the one it is operatively associated with in nature.

The term "homologous" refers to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., *Cell,* 50:667, 1987). Such proteins (and their encoding nucleic acids) have sequence homology, as reflected by their sequence similarity, whether in terms of percent identity or by the presence of specific residues or motifs and conserved positions.

For instance, referring again to particular embodiments where homologous proteins are Eta-1 polypeptides, homologous Eta-1 in closely related species of animals or, for example, between closely related species of felines (e.g., between a domesticated Abyssinian cat and a domesticated Siamese cat) typically share greater than 50% sequence identity, and more preferably share at least about 60 to 65% sequence identity. Homologous Eta-1 polypeptides between closely related species of animals may also be cross-reactive in both species of animals. Eta-1 between more divergent species of animals, such as between humans and felines (e.g., between humans and a domesticated cat) or between divergent species of felines (e.g., between a domesticated cat and a tiger) may share less sequence identity and generally are not cross-reactive in both species. The following table illustrates the sequence homologies for Eta-1 of various species.

TABLE 1

SPECIES SEQUENCE HOMOLOGIES - PERCENT HOMOLOGY

| SPECIES | FELINE Eta-1 DNA | FELINE Eta-1 PROTEIN |
|---|---|---|
| HUMAN | 80.9 | 65.5 |
| MOUSE | 68.5 | 54.8 |
| CHICKEN | 43.5 | 25.7 |

The term "sequence similarity" refers to the degree of identity or correspondence between nucleic acid or amino acid sequences that may or may not share a common evolutionary origin (see Reeck et al., supra). However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, for example, the GCG (Genetics Computer Group, Version 7, Madison, Wis.) pileup program, or using any of the programs and algorithms described above.

The terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence. The term "variant" may also be used to indicate a modified or altered gene, DNA sequence, RNA, enzyme, cell, etc. For example, the present invention relates to altered or "chimeric" RNA molecules that comprise an rRNA sequence that is altered by inserting a heterologous RNA sequence that is not naturally part of that sequence or is not naturally located at the position of that rRNA sequence. Such chimeric RNA sequences, as well as DNA and genes that encode them, are also referred to herein as "mutant" sequences. "Sequence-conservative variants" of a polynucleotide sequence are those in which a change of one or more nucleotides in a given codon position results in no alteration in the amino acid encoded at that position.

"Function-conservative variants" of a polypeptide or polynucleotide are those in which a given amino acid residue in the polypeptide, or the amino acid residue encoded by a codon of the polynucleotide, has been changed or altered without altering the overall conformation and function of the polypeptide. For example, function-conservative variants may include, but are not limited to, replacement of an amino acid with one having similar properties (for example, polarity, hydrogen bonding potential, acidic, basic, hydrophobic, aromatic and the like). Amino acid residues with similar properties are well known in the art. For example, the amino acid residues arginine, histidine and lysine are hydrophilic, basic amino acid residues and may therefore be interchangeable. Similar, the amino acid residue isoleucine, which is a hydrophobic amino acid residue, may be replaced with leucine, methionine or valine. Such changes are expected to have little or no effect on the apparent molecular weight or isoelectric point of the polypeptide. Amino acid residues other than those indicated as conserved may also differ in a protein or enzyme so that the percent protein or amino acid sequence similarity (e.g., percent identity or homology) between any two proteins of similar function may vary and may be, for example, from 70% to 99% as determined according to an alignment scheme such as the Cluster Method, wherein similarity is based on the MEGALIGN algorithm. "Function-conservative variants" of a given polypeptide also include polypeptides that have at least 60% amino acid sequence identity to the given polypeptide as determined, e.g., by the BLAST or FASTA algorithms.

Preferably, function-conservative variants of a given polypeptide have at least 75%, more preferably at least 85% and still more preferably at least 90% amino acid sequence identity to the given polypeptide and, preferably, also have the same or substantially similar properties (e.g., of molecular weight and/or isoelectric point) or functions (e.g., biological functions or activities) as the native or parent polypeptide to which it is compared. Thus, for example, in particular embodiments wherein the polypeptides are Eta-1, function-conservative variants may not only have between at least 75% and at least 90% amino acid sequence identity to a given Eta-1, but preferably also have similar properties, such as conserved domains and/or similar biological function or activities, such as actuation of dendritic and/or NIC cells.

As used herein, the term "oligonucleotide" refers to a nucleic acid, generally at least 10, preferably at least 15, and more preferably at least 20 nucleotides, preferably no more than 100 nucleotides.

Oligonucleotides can be labeled, e.g., $^{32}$P-nucleotides, or nucleotides to which a label, such as biotin or a fluorescent dye (for example, Cy3 or Cy5) has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of Eta-1, or to detect the presence of nucleic acids encoding Eta-1. In a further embodiment, an oligonucleotide of the invention can form a triple helix with an Eta-1 DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A sequence that is "complementary" to a portion of a nucleic acid refers to a sequence having sufficient complementarity to be able to hybridize with the nucleic acid and form a stable duplex. The ability of nucleic acids to hybridize will depend both on the degree of sequence complementarity and the length of the antisense nucleic acid. Generally, however, the longer the hybridizing nucleic acid, the more base mismatches it may contain and still form a stable duplex (or triplex in triple helix methods). A tolerable degree of mismatch can be readily ascertained, etc., by using standard procedures to determine the melting temperature of a hybridized complex.

The present invention provides antisense nucleic acids (including ribozymes), which may be used to inhibit expression of an Eta-1 gene or its gene product. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, triple helix interactions, ribozymes and RNase-H mediated arrest. Antisense nucleic acid molecules can be encoded by a recombinant gene for expression in a cell, or alternatively they can be prepared synthetically.

Specific non-limiting examples of synthetic oligonucleotides envisioned for this invention include, in addition to the nucleic acid moieties described above, oligonucleotides that contain phosphorothioates, phosphotriesters, methyl phosphonates, short chain alkyl, or cycloalkyl intersugar linkages or short chain heteroatomic or heterocyclic intersugar linkages. Nitrogen linkers or groups containing nitrogen can also be used to prepare oligonucleotide mimics. Also envisioned are phosphoramidate and phosphorothioamidate oligomeric compounds, and oligonucleotides having morpholino backbone structures. In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone. Other synthetic oligonucleotides may contain substituted sugar moieties comprising one of the following at the 2' position: OH, SH, SCH$_3$, F, OCN, O(CH$_2$)$_n$H$_2$ or O(CH$_2$)$_n$CH$_3$ where n is from 1 to about 10; C$_1$ to C$_{10}$ lower alkyl, substituted lower alkyl, alkaryl or aralkyl; Cl; Br; CN; CF$_3$; OCF$_3$; O—; S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; a fluorescent moiety; an RNA cleaving group; a reporter group; an intercalator; a group for improving the pharmacokinetic and/or pharmacodynamic properties of an oligonucleotide; and other substituents having similar properties. Oligonucleotides may also have sugar mimetics such as cyclobutyls or other carbocyclics in place of the pentofuranosyl group.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a T$_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher T$_m$, e.g., 40% formamide, with 5× or 6×SCC. High stringency hybridization conditions correspond to the highest T$_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of T$_m$ for hybrids of nucleic acids having those sequences. The relative stability (corresponding to higher T$_m$) of nucleic acid hybridizations decreases in the following order: RNA:RNA, DNA:RNA, DNA:DNA. For hybrids of greater than 100 nucleotides in length, equations for calculating T$_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a T$_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligoncucleotides), 55° C. (for 20-base oligonucleotides) and 60° C. (for 23-base oligonucleotides). Exemplary suitable hybridization conditions for oligonucleotides include washing in 6×SSC/ 0.05% sodium pyrophosphate, or other conditions that afford equivalent levels of hybridization.

Polypeptides and Nucleic Acids of the Present Invention

The present invention provides Eta-1 polypeptides and nucleic acids encoding the same. The Eta-1 may be derived from a feline, canine, bovine, porcine, ovine, equine, or avian species, and it is preferably derived from a feline or canine species. The sequence of the DNA encoding feline Eta-1 (SEQ ID NO: 1) is shown in FIG. 1(A), and the amino acid sequence of feline Eta-1 (SEQ ID NO: 2) is shown in FIG. 1(B). Because of the degeneracy of the genetic code (i.e., multiple codons encode certain amino acids), DNA sequences other than that shown in FIG. 1(A) can also encode the Eta-1 amino acid sequences shown in FIG. 1(B). Such other DNAs include those containing sequence conservative variations as well as function-conservative variants, as described above.

In one embodiment, the present invention provides a nucleic acid encoding feline Eta-1 which has the sequence shown in FIG. 1(A) (SEQ ID NO: 1). The nucleic acid may be DNA or RNA. Preferably, the nucleic acid is DNA, which is cDNA or genomic DNA.

The present invention also provides an oligonucleotide of at least 10 nucleotides which has a sequence complementary to a sequence present in the nucleic acid encoding the Eta-1 described above. Preferably, the oligonucleotide is at least 12, and more preferably, at least 15 or 16 nucleotides in length. In an alternate embodiment of the present invention, the oligonucleotide is detectably labeled. The detectable label may comprise any moiety capable of providing a signal, e.g., a visible signal, that the oligonucleotide is present. For example, the detectable label may be a radioisotope, a fluorophor, biotin, or a chemiluminescent or electrochemiluminescent label. In another embodiment the oligonucleotide is selectively methylated.

The present invention also provides vectors that include nucleic acids encoding Eta-1 polypeptide(s) in whole or in part. Such vectors include, for example, plasmid vectors for expression in a variety of eukaryotic and prokaryotic hosts. The vector may also further comprise an expression control sequence operably linked to the nucleic acid. The vectors of the present invention may be incorporated into a host cell.

Suitable vectors for use in practicing the present invention include, without limitation, pseudorabies virus (see, e.g., U.S. Pat. Nos. 5,240,703 and 5,047,237), bovine herpesvirus (see, e.g., U.S. Pat. Nos. 5,763,269; 5,506,128; 5,593,873), herpesvirus of turkeys (HVT; see, e.g., U.S. Pat. No. 6,121, 043), novel avian herpesvirus (a HVT/Marek's Disease chimera developed by Syntro Corporation, see, e.g., U.S. Pat. No. 5,965,138), infectious laryngotracheitis virus (a chicken herpesvirus; see, e.g., WO 95/08622), Marek's Disease virus (a poultry herpesvirus, see, e.g., WO 00/61736), equine herpesvirus (see, e.g., WO 94/03628), feline herpesvirus (see, e.g., WO 98/50069), swinepox (see, e.g., U.S. Pat. Nos. 5,382,425; 6,127,163; 6,033,904), fowlpox (see, e.g., U.S. Pat. Nos. 5,925,358; 6,136,318; 6,001,369), raccoonpox (see, e.g., WO 00/03030), and adenoviruses such as bovine, porcine or canine adenoviruses (see, e.g., WO 00/61773) and adeno-associated viruses (AAV). Other suitable viral vectors include herpes simplex virus (HSV), papillomavirus, and Epstein-Barr virus (EBV).

Suitable host cells include, without limitation, E. coli, yeast, COS cells, PC12 cells, CHO cells, GH4C1 cells, EHK-21 cells, amphibian melanophore cells, and avian host cells. Suitable vectors for the construction of naked DNA or genetic vaccinations include without limitation pTarget (Promega, Madison, Wis.), pSI (Promega, Madison, Wis.) and pcDNA (Invitrogen, Carlsbad, Calif.).

Nucleic acids encoding Eta-1 polypeptide(s) may also be introduced into cells by recombination events. For example, such a sequence is microinjected into a cell, effecting homologous recombination at the site of an endogenous gene encoding the polypeptide, an analog or pseudogene thereof, or a sequence with substantial identity to an Eta-1 polypeptide-encoding gene. Other recombination-based methods such as non-homologous recombinations, and deletion of endogenous gene by homologous recombination, especially in pluripotent cells, are also used.

Additionally, an Eta-1-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Modifications can also be made to introduce restriction sites and facilitate cloning the Eta-1 gene into an expression vector. Any technique for mutagenesis known in the art can be used, including but not limited to, in vitro site-directed mutagenesis (Hutchinson et al., *J. Biol. Chem.*, 253: 6551 (1978); Zoller and Smith, *DNA*, 3: 479–488 (1984); Oliphant et al., *Gene*, 44: 177 (1986); Hutchinson et al., *Proc. Natl. Acad. Sci. U.S.A.*, 83: 710 (1986)), use of TAB" linkers (Pharmacia), etc. PCR techniques are preferred for site directed mutagenesis (see Higuchi, 1989, "Using PCR to Engineer DNA," in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences.

Recombinant molecules can be introduced into host cells via transformation, transfection, infection, electroporation, etc., so that many copies of the gene sequence are generated.

Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of animal, can be prepared for replication in both *E. coli* and *Saccharomyces cerevisiae* by linking sequences from an *E. coli* plasmid with sequences from the yeast 2 m plasmid.

A nucleotide sequence coding for an Eta-1 polypeptide, or an antigenic fragment, derivative or analog thereof, or for a functionally active derivative thereof (including a chimeric protein) may be inserted into an appropriate expression vector, i.e., a vector which contains the necessary elements for the transcription and translation of the inserted protein-coding sequence. Thus, a nucleic acid encoding an Eta-1 polypeptide of the invention can be operationally associated with a promoter in an expression vector of the invention. Both cDNA and genomic sequences can be cloned and expressed under control of such regulatory sequences. Such vectors can be used to express functional or functionally inactivated Eta-1 polypeptides. The necessary transcriptional and translational signals can be provided on a recombinant expression vector.

Potential host-vector systems include, but are not limited to, mammalian or other vertebrate cell systems transfected with expression plasmids or infected with viruses, e.g., vaccinia and other pox viruses, adenovirus, adeno-associated virus, herpesvirus, etc.; insect cell systems infected with virus (e.g., baculovirus); microanimals such as yeast containing yeast vectors; or bacteria transformed with bacteriophage DNA, plasmid DNA, or cosmid DNA. The expression elements of vectors vary in their strengths and specificities. Depending on the host-vector system utilized, any one of a number of suitable transcription and translation elements may be used.

Expression of an Eta-1 protein may be controlled by any promoter/enhancer element known in the art, but these regulatory elements must be functional in the host selected for expression. Promoters which may be used to control Eta-1 gene expression include, but are not limited to, human cytomegalovirus immediate early promoter, pox synthetic late promoter 1, pox synthetic late promoter 2 early promoter 2, pox synthetic early promoter 2, pox O1L promoter, pox I4L promoter, pox I3L promoter, pox I2L promoter, pox I1L promoter, and pox E10R promoter.

Indeed, any type of plasmid, cosmid, YAC or viral vector may be used to prepare a recombinant nucleic acid construct which can be introduced into a cell or tissue, where expression of an Eta-1 gene product is desired. Alternatively, wherein expression of a recombinant Eta-1 gene product in a particular type of cell or tissue is desired, viral vectors that selectively infect the desired cell type or tissue type can be used.

In another embodiment, the invention provides methods for expressing Eta-1 polypeptides by using a non-endogenous promoter to control expression of an endogenous Eta-1 gene within a cell. An endogenous Eta-1 gene within a cell is an Eta-1 gene of the present invention that is ordinarily (i.e., naturally) found in the genome of that cell. A non-endogenous promoter, however, is a promoter or other nucleotide sequence that may be used to control expression of a gene but is not ordinarily or naturally associated with the endogenous Eta-1 gene. As an example, methods of homologous recombination may be employed (preferably using non-protein encoding Eta-1 nucleic acid sequences of the invention) to insert an amplifiable gene or other regulatory sequence in the proximity of an endogenous Eta-1 gene. The inserted sequence may then be used, e.g., to provide for higher levels of Eta-1 gene expression than normally occurs in that cell, or to overcome one or more mutations in the endogenous Eta-1 regulatory sequences which prevent normal levels of Eta-1 gene expression. Such methods of homologous recombination are well known in the art. See, for example, International Patent Publication Nos. WO 91/06666, WO 91/09955 and WO 90/14092.

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

A wide variety of host/expression vector combinations may be employed in expressing the DNA sequences of this invention. Useful expression vectors, for example may consist of segments of chromosomal, non-chromosomal and synthetic DNA sequences. Viral vectors commonly used in vivo or ex vivo targeting and therapy procedures are DNA-based vectors and retroviral vectors. Methods for constructing and using viral vectors are known in the art (see, e.g., Miller and Rosman, *BioTechniques* 1992, 7: 980–990). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques of genetic manipulation or by treatment with mutagenic agents. Preferably, the replication defective virus retains the sequences of its genome which are necessary for encapsidating the viral particles.

Various companies produce viral vectors commercially, including Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), Intro-Gene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), Transgene (Strasbourg, France; adenoviral, vaccinia, retroviral, and lentiviral vectors) and Invitrogen (Carlsbad, Calif.).

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner et al., *Proc. Natl. Acad. Sci. U.S.A.* 1987, 84: 7413–7417; Felgner and Ringold, *Science*, 337: 387–388 (1989); Ulmer et al., *Science*, 259: 1745–1748 (1993)). Useful lipid compounds and compositions for transfer of nucleic acids are described in International Patent Publication Nos. WO 95/18863 and WO 96/17823, and in U.S. Pat. No. 5,459,127. Lipids may be chemically coupled to other molecules for the purpose of targeting (see Mackey et al., *Proc. Natl. Acad. Sci. U.S.A.* 1988, 85: 8027–8031). Targeted peptides, e.g., hormones or neurotransmitters, and proteins such as antibodies, or non-peptide molecules could be coupled to liposomes chemically. Other molecules are also useful for facilitating transfection of a nucleic acid in vivo, such as a cationic oligopeptide or catronic polymer (e.g., International Patent Publication No. WO 95/21931), or peptides derived from DNA binding proteins (e.g., International Patent Publication No. WO 96/25508).

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., *J. Biol. Chem.*, 267: 963–967(1992); Wu and Wu, *J. Biol. Chem.*, 263: 14621–14624 (1988); Hartmut et al., Canadian Patent Application No. 2,012,311, Williams et al., *Proc. Natl. Acad. Sci. U.S.A.* 1991, 88: 2726–2730). Receptor-mediated DNA delivery approaches can also be used (Curiel et al., *Hum. Gene Ther.*, 3: 147–154 (1992); Wu and Wu, *J. Biol. Chem.*, 262: 4429–4432 (1987)). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., *C.P. Acad. Sci.*, 321: 893 (1998); WO 99/01157, WO 99/01158; WO 99/01175).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, *Nat. Med.*, 1: 887–889 (1995)). In that regard, it is advantageous to employ a viral vector that is engineered to express a minimal number of antigens.

Purification of Eta-1 polypeptides from natural or recombinant sources is achieved by methods well-known in the art. For example, Eta-1 polypeptides and proteins can be purified by various methods including, without limitation, preparative disc-gel electrophoresis, isoelectric focusing, HPLC, reverse-phase HPLC, gel filtration, ion exchange and partition chromatography, precipitation and salting-out chromatography, extraction, and countercurrent distribution. For some purposes, it may be preferable to produce the polypeptide in a recombinant system in which the protein contains an additional sequence tag that facilitates purification. The polypeptide can then be purified from a crude lysate of the host cell by chromatography on an appropriate solid-phase matrix. Alternatively, antibodies produced against the protein or against peptides derived therefrom can be used as purification reagents. In a preferred embodiment, Eta-1 is obtained by constructing a recombinant DNA sequence comprising the coding region for Eta-1 fused in frame to a sequence encoding a 6 C-terminal histidine residues in the pSFV1 replicon (GIBCO/BRL). mRNA encoded by this plasmid is synthesized using techniques well-known to those skilled in the art and introduced into BHK-21 cells by electroporation. The cells synthesize and secrete mature Eta-1 polypeptides containing 6 C-terminal histidine. The modified Eta-1 polypeptides are purified from the cell supernatant by affinity chromatography using a histidine-binding resin (His-bind, Novagen, Madison, Wis.). Eta-1 may also be expressed in bacteria or yeast and purified using techniques well-known to those in the art, e.g., the use of a His-tag and appropriate metal-chelate affinity column to purify the protein.

Eta-1 polypeptides isolated from any source may be modified by methods known in the art. For example, Eta-1 polypeptides are phosphorylated or dephosphorylated, glycosylated or deglycosylated, and the like. Especially useful are modifications that alter solubility, stability, and binding specificity and affinity.

Accordingly, the present invention provides Eta-1 polypeptides isolated naturally or recombinantly. In a preferred embodiment, the polypeptides of the invention are derived from a feline and have a molecular weight of approximately 50–60 kDa. Feline Eta-1 was expressed as a his-tagged (C-terminal) fusion protein in a eukaryotic poxvirus expression system. Supernatants were collected from EKS-4 cells infected with the poxvirus expressing Eta-1. Eta-1 protein was detected at 24 hours post infection and increased over 72 hours. Western blot analysis of supernatants from infected ESK-4 cells showed an anti-Eta-1 reactive band (anti-human Eta polyclonal) at approximate 50–55 kDa. Sequence analysis predicts a 299 amino acid protein containing two N-linked glycosylation sites and an RGD peptide. Feline Eta-1, like its human and mouse counterparts, is expected to be phosphorylated. The hydrophilicity plot shows that the protein has a signal peptide sequence and is highly hydrophilic, indicating secretion. The sequence predicts an isoelectric point of 4.428. The characterization of the polypeptides of the invention is based, at least in part, on the ability of the polypeptide to support adhesion of T cells and macrophages.

The invention also contemplates fragments of Eta-1 polypeptides. A "fragment" preferably retains at least a portion of the biological activity of the corresponding full-length polypeptides, e.g., at least 50% activity, preferably at least 75%, and most preferably, at least 90%. Alternatively, a fragment of the invention may also exhibit enhanced activity relative to the full-length polypeptide, e.g., at least twice as much, more than ten times as much, preferably more than fifty times as much, and most preferably at least 100 times the biological activity of the corresponding full-length polypeptide.

The present invention also encompasses the production of chimeric molecules made from fragments of Eta-1 polypeptide in any combination. For example, a chimeric molecule may be made that comprises fragments of Eta-1 polypeptides from two or more species.

Furthermore, the present invention also encompasses antibodies that are specific for Eta-1 polypeptides identified as described above. The antibodies are polyclonal or monoclonal, and discriminate Eta-1 from different species, identify functional domains, and the like. Such antibodies are conveniently made using the methods and compositions described in Harlow and Lane, *Antibodies: A Laboratory Manual*, Cold Spring Harbor Laboratory, Cold Spring Harbor, N.Y. (1988) (hereinafter "Harbor & Lane"), as well as immunological and hybridoma technologies known to those skilled in the art. Where natural or synthetic Eta-1 peptides are used to induce an Eta-1 specific immune response, the peptides are conveniently coupled to a suitable carrier, such as KLH, and administered in a suitable adjuvant, such as Freund's. Preferably, selected peptides are coupled to a lysine core carrier substantially according to the methods of Tan, *Proc. Natl. Acad. Sci. USA*, 85: 5049–5413 (1988). The resulting antibodies, especially internal imaging anti-idiotypic antibodies, are also prepared using known methods.

In one embodiment, purified Eta-1 is used to immunize mice, after which their spleens are removed, and splenocytes used to form cell hybrids with myeloma cells to obtain clones of antibody-secreting cells according to techniques that are standard in the art. The resulting monoclonal antibodies secreted by such cells are screened using in vitro assays for biological activity, including but not limited to, binding to flt-3 receptor.

Anti-Eta-1 antibodies are used to identify and quantify Eta-1, using immunoassays such as ELISA, RIA, and the like. In addition, these antibodies can be used to identify, isolate and purify from different sources, and to perform subcellular and histochemical localization studies.

Antibodies to Eta-1 are useful, inter alia, for diagnostics and intracellular regulation of Eta-1 activity, as set forth below. According to the invention, Eta-1 polypeptides produced, e.g., recombinantly or by chemical synthesis, and fragments or other derivatives or analogs thereof, including fusion proteins, may be used as an immunogen to generate antibodies that recognize the Eta-1 polypeptide. Such antibodies include, but are not limited to, polyclonal, monoclonal, chimeric, single chain, Fab fragments, and a Fab expression library. Such an antibody is preferably specific for (i.e., specifically binds to) a feline Eta-1 polypeptide of the present invention. However, the antibody may, alternatively, be specific for an Eta-1 ortholog from some other species of animal, preferably another species of feline. The antibody may recognize a mutant form of Eta-1, or wild-type Eta-1, or both.

Various procedures known in the art may be used for the production of polyclonal antibodies to Eta-1 polypeptide or derivative or analog thereof. For the production of antibody, various host animals can be immunized by injection with the Eta-1 polypeptide, or a derivative (e.g., fragment or fusion protein) thereof, including but not limited to rabbits, mice, rats, sheep, goats, etc. In one embodiment, the Eta-1 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species.

For preparation of monoclonal antibodies directed toward the Eta-1 polypeptide, or fragment, analog, or derivative thereof, any technique that provides for the production of antibody molecules by continuous cell lines in culture may be used. These include, but are not limited to, the hybridoma technique originally developed by Kohler and Milstein (*Nature*, 256: 495–497 (1975)), as well as the trioma technique, the human B-cell hybridoma technique (see, e.g., Kozbor et al., *Immunology Today*, 4: 72 (1983); and the EBV-hybridoma technique (Cole et al., in *Monoclonal Antibodies and Cancer Therapy*, Alan R. Liss, Inc., pp. 77–96 (1985)). In an additional embodiment of the invention, monoclonal antibodies can be produced in germ-free animals (International Patent Publication No. WO 89/12690). In fact, according to the invention, techniques developed for the production of "chimeric antibodies" (Morrison et al., *J. Bacteriol.*, 159: 870; Neuberger et al., *Nature*, 312: 604–608 (1984); Takeda et al., *Nature*, 314: 452–454 (1985)) may also be used. Briefly, such techniques comprise splicing the genes from an antibody molecule from a first species of animal (e.g., a cat) that is specific for an Eta-1 polypeptide together with genes from an antibody molecule of appropriate biological activity derived from a second species of animal (e.g., from a human). Such chimeric antibodies are within the scope of this invention.

Antibody fragments which contain the idiotype of the antibody molecule can be generated by known techniques. For example, such fragments include, but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

According to the invention, techniques for the production of single chain antibodies (see, e.g., U.S. Pat. Nos. 5,476, 786, 5,132,405, and 4,946,778) can be adapted to produce Eta-1 polypeptide-specific single chain antibodies. An additional embodiment of the invention utilizes the techniques described for the construction of Fab expression libraries (Huse et al., *Science*, 246: 1275–1281 (1989)) to allow rapid and easy identification of monoclonal Fab fragments with the desired specificity for an Eta-1 polypeptide, or its derivatives, or analogs.

In the production and use of antibodies, screening for or testing with the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an Eta-1 polypeptide, one may assay generated hybridomas for a product which binds to an Eta-1 polypeptide fragment containing such epitope. For selection of an antibody specific to an Eta-1 polypeptide from a particular species of animal, one can select on the basis of positive binding with Eta-1 polypeptide expressed by or isolated from cells of that species of animal.

The foregoing antibodies can be used in methods known in the art relating to the localization and activity of the Eta-1 polypeptide, e.g., for Western blotting, imaging Eta-1 polypeptide in situ, measuring levels thereof in appropriate physiological samples, or using any of the detection techniques mentioned above or known in the art. Such antibodies can also be used in assays for ligand binding, e.g., as described in U.S. Pat. No. 5,679,582. Antibody binding generally occurs most readily under physiological conditions, e.g., pH of between about 7 and 8, and physiological ionic strength. The presence of a carrier protein in the buffer solutions stabilizes the assays. While there is some tolerance of perturbation of optimal conditions, e.g., increasing or decreasing ionic strength, temperature, or pH, or adding detergents or chaotropic salts, such perturbations will decrease binding stability.

In still other embodiments, anti-Eta-1 antibodies may also be used to isolate cells which express an Eta-1 polypeptide by panning or related immunoadsorption techniques.

In a specific embodiment, antibodies that agonize or antagonize the activity of an Eta-1 polypeptide can be generated. In particular, intracellular single chain Fv antibodies can be used to regulate (inhibit) Eta-1 activity (Marasco et al., *Proc. Natl. Acad. Sci. U.S.A.* 1993, 90: 7884–7893; Chen, *Mol. Med. Today*, 3: 160–167 (1997); Spitz et al., *Anticancer Res.*, 16: 3415–22 (1996); Indolfi et al., *Nat. Med.*, 2: 634–635 (1996); Kijma et al., *Pharmacol. Ther.*, 68: 247–267 (1995)). Such antibodies can be tested using the assays described infra for identifying ligands.

Applications and Uses

Described herein are various applications and uses for Eta-1 nucleic acids, Eta-1 polypeptides, and antibodies directed against Eta-1 polypeptides. As described, e.g., in the Examples, infra, the Eta-1 of the present invention may induce or enhance an immune response in an animal. In particular, without being bound by any particular theory or mechanism of action, the molecules of the invention support adhesion of T cells and macrophages. As a result, the presence or release of Eta-1 at a site in an animal can stimulate an immune response by activating those cell types and drawing them to the site of Eta-1 release. Eta-1 will also affect an immune response through the activation of dendritic cells, natural killer cells and T-lymphocytes (CD4+ and CD8+), and through the induction of Th1 cytokines (IL-12, IL-18, IFNgamma).

Accordingly, the Eta-1 nucleic acids, polypeptides and antibodies of the present invention may be used in prognostic and diagnostic applications to identify or detect an immune response stimulated by an Eta-1. The Eta-1 nucleic acids, polypeptides and antibodies of the invention may also be used in screening assays, e.g., to identify compounds, such as an Eta-1 receptor that specifically bind to an Eta-1 of the invention or, alternatively, to identify compounds that modulate binding of an Eta-1 to an Eta-1 receptor or other molecule. Such compounds may be useful, e.g., as immune enhancing or suppressing drugs.

The Eta-1 nucleic acids and polypeptides of the invention may also be used in pharmaceutical preparations. For example, in a particularly preferred embodiment of the invention, an Eta-1 polypeptide or Eta-1 nucleic acid of the invention is used in a vaccine or in a cancer therapy, e.g., as an adjuvant to enhance an immune response to the vaccine or tumor antigen. In a preferred embodiment, the nucleic acids and polypeptides of the invention are used in a vaccine or therapy for administration to cats and/or dogs. In this regards, the molecules of the present invention may be administered as a DNA vaccine as a means for gene therapy. Alternatively, the molecules of the invention may be administered as a viral vector or subunit protein.

Diagnostic Applications

A variety of methods can be employed for diagnostic and prognostic methods using reagents such as the Eta-1 nucleic acids and polypeptides described supra (including fragments, chimeras and fusions thereof), as well as antibodies directed against these polypeptides. For example, by using the methods described here to detect an Eta-1 nucleic acid or an Eta-1 polypeptide in an individual, it is possible to detect, in the individual, the presence or absence of an immune response associated with an Eta-1. Alternatively, the prognostic and diagnostic methods described here may be used in the prognostic or diagnostic evaluation of a disease or disorder, e.g., an immune disorder that is associated with an Eta-1. Specific applications of such methods include, but are not limited to: (1) the detection of either over- or underexpression of an Eta-1 gene product (e.g., an Eta-1 mRNA) relative to expression in an unaffected state; (2) the detection of either and over- or an under-abundance of an Eta-1 gene product relative to abundance in an unaffected state; and (3) the detection of an aberrant Eta-1 gene product activity relative to the unaffected state.

In preferred embodiments, the methods described herein are performed using pre-packaged diagnostic kits. Such kits may comprise at least one specific Eta-1 nucleic acid or an Eta-1 specific antibody reagent of the invention. The kit and any reagent(s) contained therein can be used, for example, in a clinical setting, to diagnose animals exhibiting abnormalities, such as an immune disorder.

A sample comprising a nucleated cell (of any cell type) from an individual may be used in such diagnostic and prognostic methods as a starting source for genomic nucleic acid and to detect mutations of an Eta-1 gene. A sample comprising a cell of any cell type or tissue of any tissue type in which an Eta-1 gene is expressed may also be used in such diagnostic methods, e.g., for detection of Eta-1 gene expression or of Eta-1 gene products (such as Eta-1 proteins), as well as for identifying cells, particularly hemopoietic cells, that express an Eta-1 gene or an Eta-1 gene product.

Detection of Eta-1 Nucleic Acid

For the detection of Eta-1 mutations or to assay levels of Eta-1 nucleic acid sequences in a sample, a variety of methods may be employed. For example, mutations within an Eta-1 gene may be detected by utilizing a number of techniques known in the art and with nucleic acid derived from any nucleated cell. The nucleic acid may be isolated according to standard nucleic acid preparation procedures that are already well known to those of skill in the art.

Eta-1 nucleic acid sequences may be used in hybridization or amplification assays of such biological samples to detect abnormalities involving Eta-1 gene structure. Exemplary abnormalities that can be detected in such methods include point mutations, single nucleotide polymorphisms (SNPs), insertions, deletions, inversions, translocations and chromosomal rearrangements. Exemplary assays that can be used to detect these abnormalities include Southern analyses, fluorescence in situ hybridization (FISH), single-stranded conformational polymorphism analyses (SSCP) and polymerase chain reaction (PCR) analyses.

As an example, and not by way of limitation, diagnostic methods for the detection of Eta-1 gene-specific mutations can involve contacting and incubating nucleic acids (including recombinant DNA molecules, clones genes or degenerate variants thereof) obtained from a sample with one or more labeled nucleic acid reagents, such as recombinant Eta-1 DNA molecules, cloned genes or degenerate variants thereof, under conditions favorable for specifically annealing or hybridizing these reagents to their complementary sequences in the sample nucleic acids. Preferably, the lengths of these nucleic acid reagents are at least 15 to 30 nucleotides. After incubation, all non-annealed or non-hybridized nucleic acids are removed. The presence of nucleic acids that have hybridized, if any such molecules exist, is then detected and the Eta-1 gene sequences to which the nucleic acid reagents have annealed may be compared to the annealing pattern expected from a normal (i.e., a wild-type) Eta-1 gene sequence in order to determine whether an Eta-1 gene mutation is present.

In a preferred embodiment of such a detection scheme, the nucleic acid from the cell type or tissue of interest may be immobilized, for example, to a solid support such as a membrane or a plastic surface (for example, on a nylon membrane, a microtiter plate or on polystyrene beads). After incubation, non-annealed, labeled Eta-1 nucleic acid reagents may be easily removed and detection of the remaining, annealed, labeled Eta-1 nucleic acid reagents may be accomplished using standard techniques that are well-known in the art.

Alternative diagnostic methods for the detection of Eta-1 gene specific nucleic acids in patient samples or in other cell sources may involve their amplification, e.g., by PCR followed by detection of the amplified molecules using techniques that are well known to those of skill in the art. The resulting amplified sequences may be compared to those that would be expected if the nucleic acid being amplified contained only normal copies of an Eta-1 gene in order to determine whether an Eta-1 mutation is present in the samples.

Other well-known genotyping techniques may also be used to identify individuals carrying Eta-1 mutations. Such techniques include, for example, the use of restriction fragment length polymorphisms (RFLPs). Other methods which may be used to identify Eta-1 mutations capitalize on the presence of variable numbers of short tandemly repeated DNA sequences between the restriction enzyme sites. For example, U.S. Pat. No. 5,075,217 describes a DNA marker based on length polymorphisms in blocks of short tandem repeats. The average separation of such blocks is estimated to be 30 to 70 kb. Markers that are so closely spaced exhibit a high frequency of co-inheritance and are extremely useful in the identification of genetic mutations, including for example mutations within the Eta-1 gene, as well as for the diagnosis of diseases and disorders related to such genetic mutations.

The diagnostic and prognostic methods of the invention also include methods for assaying the level of Eta-1 gene expression. For example, RNA from a cell type or tissue, such as hemopoietic cells, that is known or suspected to express the Eta-1 gene may be isolated and tested utilizing hybridization or PCR techniques such as those described supra. The isolated cells may be, for example, cells derived from a cell culture or from an individual. The analysis of cells taken from a cell culture may be useful, e.g., to test the effect of compounds on the expression of an Eta-1 gene, or alternatively, to verify that the cells are ones of a particular cell type that expresses an Eta-1 gene.

In one preferred embodiment of such a detection scheme, a cDNA molecule is synthesized from an RNA molecule of interest (e.g., by reverse transcription). A sequence within the cDNA may then be used as a template for a nucleic acid amplification reaction such as PCR. Nucleic acid reagents used as synthesis initiation reagents (e.g., primers) in the reverse transcription and amplification steps of such an assay are preferably chosen from the Eta-1 nucleic acid sequences described herein or are fragments thereof. Preferably, the nucleic acid reagents are at least about 9 to 30 nucleotides in length. The amplification may be performed using, e.g., radioactively labeled or fluorescently labeled nucleotides, for detection. Alternatively, enough amplified product may be made such that the product can be visualized by standard ethidium bromide or other staining methods.

Eta-1 gene expression assays of the invention may also be performed in situ (i.e., directly upon tissue sections of patient tissue, which may be fixed and/or frozen), thereby eliminating the need of nucleic acid purification. Eta-1 nucleic acid reagents may be used as probes or as primers for such in situ procedures (see, e.g., Nuovo, *PCR In Situ Hybridization: Protocols And Application,* Raven Press, New York (1992)). Alternatively, if a sufficient quantity of the appropriate cells can be obtained, standard Northern analysis can be performed to determine the level of Eta-1 gene expressed by detecting levels of Eta-1 mRNA.

Detection of Eta-1 Gene Products

The diagnostic and prognostic methods of the invention also include detecting levels of an Eta-1 protein or other Eta-1 polypeptide, including functionally conserved variants and fragments thereof. For example, antibodies directed against unimpaired, wild-type or mutant Eta-1 gene products or against functionally conserved variants or peptide fragments of an Eta-1 gene product may be used as diagnostic and prognostic reagents for immune disorders or, alternatively, to detect an immune response associated with an Eta-1. Such reagents may be used, for example, to detect abnormalities in the level of Eta-1 gene product synthesis or expression, or to detect abnormalities in the structure, temporal expression or physical location of an Eta-1 gene product. Antibodies and immunoassay methods such as those described herein below also have important in vitro applications for assessing the efficacy of treatments, e.g., for immune disorders. Such antibodies and immunoassays also have important applications for assessing efficacy of vaccines, e.g., by assaying a vaccine's ability to stimulate an immune response. For example, antibodies, or fragments of antibodies, can be used in screens of potentially therapeutic compounds in vitro to ascertain a compound's effects on Eta-1 gene expression and Eta-1 polypeptide production. Compounds that may have beneficial effects on an Eta-1 associated disorder can be identified and a therapeutically effective dose for such compounds may be determined using such assays.

In vitro immunoassays can also be used to assess the efficacy of cell-based gene therapy for an Eta-1 associated disorder. For example, antibodies directed against Eta-1 polypeptides may be used in vitro to determine the level of Eta-1 gene or polypeptide expression achieved in cells genetically engineered to produce an Eta-1 polypeptide. Such methods may be used to detect intracellular Eta-1 gene products, preferably using cell lysates or extracts, to detect expression of Eta-1 gene products of cell surfaces, or to detect Eta-1 gene products secreted into the cell culture media. Such an assessment can be used to determine the number of transformed cells necessary to achieve therapeutic efficacy in vivo, as well as optimization of the gene replacement protocol.

Generally the tissue or cell types analyzed using such methods will include ones, such as hematopoietic cells, that are known to express an Eta-1 gene product. Protein isolation methods such as those described by Harlow & Lane, supra, may be employed. The isolated cells may be cells derived from cell culture or from an individual (e.g., an animal suspected of having an Eta-1 associated disorder or suspected of having a propensity for an Eta-1 associated disorder).

As one example, antibodies or fragments of antibodies may be used to detect the presence of an Eta-1 gene product, a variant of an Eta-1 gene product or fragments thereof, for example, by immunofluorescence techniques employing a fluorescently labeled antibody coupled with light microscopic, flow cytometric or fluorimetric detection methods.

Antibodies or fragments thereof may also be employed histologically, for example in immunofluorescence or immunoelectron microscopy techniques, for in situ detection of an Eta-1 gene product. In situ detection may be accomplished by removing a histological specimen (e.g., a tissue sample) from an animal and applying thereto a labeled antibody of the present invention or a fragment of such an antibody. The antibody or antibody fragment is preferably applied by overlaying the labeled antibody or antibody fragment onto a biological sample. Through the use of such a procedure, it is possible to detect, not only the presence of an Eta-1 gene product, but also the gene product's distribution in the examined tissue. A wide variety of histological methods that are well known in the art (for example, staining procedures) can be readily modified by those skilled in the art without undue experimentation to achieve such in situ detection.

Immunoassays for Eta-1 gene products will typically comprise incubating a biological sample (for example, a biological fluid, a tissue extract, freshly harvested cells or cell lysates) in the presence of a detectably labeled antibody that is capable of specifically binding an Eta-1 gene product (including, for example, a functionally conserved variant or a peptide fragment thereof). The bound antibody may then be detected by any of a number of techniques well known in the art.

Screening Assays

Using screening assays such as those described herein, it is also possible to identify compounds that bind to or otherwise interact with an Eta-1 gene product, including intracellular compounds (for example, proteins or portions of proteins) that interact with an Eta-1 gene product, natural and synthetic ligands (or receptors) for an Eta-1 gene product, compounds that interfere with the interaction of an Eta-1 gene product (for example, compounds that interfere with specific binding of an Eta-1 gene product to a receptor or intracellular compound), and compounds that modulate the activity of an Eta-1 gene (for example, by modulating the level of Eta-1 gene expression) or the activity (for example, the bioactivity) of an Eta-1 polypeptide or other Eta-1 gene products.

For example, and without being bound by any particular theory or mechanism of action, the Eta-1 of the invention is believed to specifically bind to a flt-3 receptor expressed by certain types of cells. Such binding is believed to activate those cells expressing the flt-3 receptor and attract or draw those cells to the site where an Eta-1 gene product is present or secreted (i.e., to the site where concentration of an Eta-1 gene product is highest), thereby stimulating an immune response. Thus, the screening methods of the present invention may be used to identify receptors and cells expressing receptors, that specifically bind to and are thereby activated by an Eta-1 gene product of the invention. The screening methods may also be used to identify compounds that inhibit or modulate such a binding interaction and are therefore useful as an agonist or antagonist for Eta-1 binding to an Eta-1 specific receptor. In particular, such compounds may be used, e.g., to enhance or suppress an Eta-1 associated immune response.

Alternatively, the screening assays described here may be used to identify compounds that bind to a promoter or other regulatory sequence of an Eta-1 gene, and so may modulate the level of Eta-1 gene expression (see, e.g., Platt, *J. Biol. Chem.*, 269: 28558–28562 (1994)).

Classes of compounds that may be identified by such screening assays include, but are not limited to, small molecules (e.g., organic or inorganic molecules which are less than about 2 kDa in molecular weight, are more preferably less than about 1 kDa in molecular weight, and/or are able to cross the blood-brain barrier or gain entry into an appropriate cell and affect expression of either an Eta-1 gene or of some gene involved in an Eta-1 regulatory pathway) and macromolecules (e.g., molecules greater than about 2 kDa in molecular weight). Compounds identified by these screening assays may also include peptides and polypeptides, phosphopeptides, antibodies and antibody fragments.

Assays for Binding Compounds

In vitro systems can be readily designed to identify compounds capable of binding the Eta-1 gene products of the present invention. Such compounds can be useful, for example, in modulating the activity of a wild-type Eta-1 gene product or, alternatively, to modulate the activity of a mutant or other variant Eta-1 gene product.

Generally, such screening assays involve preparation of a reactive mixture comprising an Eta-1 gene product and a test compound under conditions and for a time sufficient to allow the two compounds to interact (e.g., bind), thereby forming a complex that may be detect. The assays may be conducted in any of a variety of different ways. For example, one embodiment comprises anchoring an Eta-1 polypeptide or a test compound onto a solid phase and detecting complexes of the Eta-1 polypeptide and the test compound that are on the solid phase at the end of the reaction and after removing (e.g., by washing) unbound compounds. For example, an Eta-1 gene product may be anchored onto a solid surface and a labeled compound (e.g., labeled according to any of the methods described supra) is contacted to the surface. After incubating the test compound for a sufficient time and under sufficient conditions that a complex may form between the Eta-1 gene product and the test compound, unbound molecules of the test compound are removed from the surface and labeled molecules which remain are detected.

In another, alternative embodiment, molecules of one or more different test compounds are attached to the solid phase and molecules of a labeled Eta-1 polypeptide may be contacted thereto. In such embodiments, the molecules of different test compounds are preferably attached to the solid phase at a particular location on the solid phase so that test compounds that bind to an Eta-1 polypeptide may be identified by determining the location of bound Eta-1 polypeptides on the solid phase or surface.

Assays for Compounds that Interact with Eta-1

Any of a variety of known methods for detecting protein-protein interactions may also be used to detect and/or identify proteins that interact with an Eta-1 gene product. For example, co-immunoprecipitation, cross-linking and co-purification through gradients or chromatographic columns as well as other techniques known in the art may be employed. Proteins which may be identified using such assays include, but are not limited to, extracellular proteins, such as Eta-1 specific receptors, as well as intracellular proteins such as signal transducing proteins.

For example, an expression cloning assay may be used to identify Eta-1 specific receptors and other proteins that specifically interact with an Eta-1 gene product. In such assays, a cDNA expression library may be generated from any cell line that expresses an Eta-1 specific receptor. Clones from such an expression library may then be transfected or infected into cells that do not normally express an Eta-1 specific receptor. Cells that are transfected with a clone that encodes an Eta-1 specific receptor may then express this gene product, and can be identified and isolated using standard techniques such as FACS or using magnetic beads that have an Eta-1 polypeptide.

Alternatively, an Eta-1 specific receptor may be isolated from a cell line, including any of the Eta-1 receptor expressing cell lines recited above, using immunoprecipitation techniques that are well known in the art.

Eta-1 specific receptors may also be isolated using any of the screening assays discussed supra for identifying Eta-1 binding compounds. For example, an Eta-1-Fc fusion polypeptide may be bound or otherwise attached to a solid surface, and a labeled compound (e.g., a candidate Eta-1 receptor) may be contacted to the surface for a sufficient time and under conditions that permit formation of a complex between the Eta-1-Fc fusion polypeptide and the test compound. Unbound molecules of the test compound can then be removed from the surface (e.g., by washing), and labeled compounds that remain bound can be detected.

Once isolated, standard techniques may be used to identify any protein detected in such assays. For example, at least a portion of the amino acid sequence of a protein that interacts with the Eta-1 gene product can be ascertained using techniques well known in the art, such as the Edman degradation technique (see, e.g., Creighton, Proteins: Structures and Molecular Principles, W.H. Freeman & Co., NY, 1983, pp. 34–49).

Once such proteins have been identified, their amino acid sequence may be used as a guide for the generation of oligonucleotide mixtures to screen for gene sequences encoding such proteins; e.g., using standard hybridization or PCR techniques described supra. See, for example, Ausubel supra; and PCR Protocols: A Guide to Methods and Applications, Imis et al., eds., Academic Press, Inc., New York (1990) for descriptions of techniques for the generation of such oligonucleotide mixtures and their use in screening assays.

Other methods are known in the art which result in the simultaneous identification of genes that encode a protein that interacts with an Eta-1 polypeptide. For example, expression libraries may be probed with a labeled Eta-1 polypeptide.

As another example, a two-hybrid system may be used to detect protein interactions with an Eta-1 gene product in vivo. Briefly, utilizing such a system, plasmids may be constructed which encode two hybrid proteins: one of which preferably comprises the DNA-binding domain of a transcription activator protein fused to an Eta-1 gene product. The other hybrid protein preferably comprises an activation domain of the transcription activator protein used in the first hybrid, fused to an unknown protein that is encoded by a cDNA recombined into the plasmid library as part of a cDNA library. Both the DNA-binding domain fusion plasmid and the cDNA library may be co-transformed into a strain of *Saccharomyces cerevisiae* or other suitable animal which contains a reporter gene (for example, HBS, lacZ, HIS3 or GFP). Preferably, the regulatory region of this reporter gene comprises a binding site for the transcription activator moiety of the two hybrid proteins. In such a two-hybrid system, the presence of either of the two hybrid proteins alone cannot activate transcription of the reporter gene. Specifically, the DNA-binding domain hybrid protein cannot activate transcription because it cannot localize to the necessary activation function. Likewise, the activation domain hybrid protein cannot activate transcription because it cannot localize to the DNA binding site on the reporter gene. However, interaction between the two hybrid proteins, reconstitutes that functional transcription activator protein and results in expression of the reporter gene. Thus, in a two-hybrid system, such as the one described here in detail, an interaction between an Eta-1 polypeptide (i.e., the Eta-1 polypeptide fused to the transcription activator's DNA binding domain) and a test polypeptide (i.e., a protein fused to the transcription activator's DNA binding domain) may be detected by simply detecting expression of a gene product of the reporter gene.

Once compounds have been identified which bind to an Eta-1 gene product of the invention, the screening methods described in these methods may also be used to identify other compounds (e.g., small molecules, peptides and proteins) that bind to these binding compounds. Such compounds may also be useful to modulating Eta-1-related bioactivities, for example by binding to a natural Eta-1 receptor or binding partner, and presenting its interaction with an Eta-1 gene product. For instance, these compounds could be tested for their ability to inhibit the binding of Eta-1-Fc to cell lines which express Eta-1 specific receptor.

Assays for Compounds that Interfere with an Eta-1-Receptor Interaction

As noted supra, an Eta-1 gene product of the invention may interact with one or more molecules (i.e., receptors) in vivo or in vitro. Compounds that disrupt or otherwise interfere with this binding interaction are therefore useful in modulating activity of an Eta-1 gene product, and, in particular, may serve to enhance or suppress an immune response associated with an Eta-1 gene or gene product of the invention.

Such compounds include, but are not limit to, compounds identified according to the screening assays described supra, for identifying compounds that bind to an Eta-1 gene product, including any of the numerous exemplary classes of compounds described therein.

In general, assays for identifying compounds that interfere with the interaction between an Eta-1 gene product and a binding partner (e.g., a receptor) involve preparing a test reaction mixture that contains the Eta-1 gene product and its binding partner under conditions and for a time sufficient for the Eta-1 gene product and its binding partner to bind and form a complex. In order to test a compound for inhibitory activity (i.e., for the ability to inhibit formation of the binding complex or to disrupt the binding complex once formed), the test compound preferably is also present in the test reaction mixture. The test compound may be initially included in the test reaction mixture with the Eta-1 gene product and its binding partner, or the test compound may be added to the test reaction mixture subsequent to the addition of the Eta-1 gene product and its binding partner. In preferred embodiments, one or more control reaction mixtures may also be prepared. Typically, a control reaction mixture will contain the same Eta-1 gene product and binding partner that are in the test reaction mixture, but will not contain a test compound. A control reaction mixture may also contain a placebo, not present in the test reaction mixture, in place of the test compound. The formation of a complex between the Eta-1 gene product and the binding partner may then be detected in the reaction mixture. The formation of such a complex in the absence of the test compound but not in the presence of the test compound, indicates that the test compound is one which interferes with or modulates the interaction of an Eta-1 polypeptide and a binding partner.

Such assays for compounds that modulate the interaction of an Eta-1 gene product and a binding partner may be conducted in a heterogenous format or, alternatively, in a homogeneous format. Heterogeneous assays typically involve anchoring either an Eta-1 gene product or a binding partner onto a solid phase and detecting compounds anchored to the solid phase at the end of the reaction. Thus, such assays are similar to the solid phase assays described supra for detecting and/or identifying Eta-1 nucleic acids and gene products and for detecting or identifying Eta-1 binding partners. Indeed, those skilled in the art will recognize that many of the principles and techniques described above for those assays may be modified and applied without undue experimentation in the solid phase assays described here, for identifying compounds that modulate interaction(s) between and Eta-1 gene product and a binding partner.

Regardless of the particular assay used, the order to which reactants are added to a reaction mixture may be varied; for example, to identify compounds that interfere with the interaction of an Eta-1 gene product with a binding partner by competition, or to identify compounds that disrupt a preformed binding complex. Compounds that interfere with the interaction of an Eta-1 gene product with a binding partner by competition may be identified by conducting the reaction in the presence of a test compound. Specifically, in such assays, a test compound may be added to the reaction mixture prior to or simultaneously with the Eta-1 gene product and the binding partner. Test compounds that disrupt preformed complexes of an Eta-1 gene product and a binding partner may be tested by adding the test compound to a reaction mixture after complexes have been formed.

The screening assays described herein may also be practiced using peptides or polypeptides that correspond to portions of a full length Eta-1 polypeptide or protein, or with fusion proteins comprising such peptide or polypeptide sequences. For example, screening assays for identifying compounds the modulate interactions of an Eta-1 polypeptide with a binding partner may be practiced using peptides or polypeptides corresponding to particular regions or domains of a full length Eta-1 polypeptide that bind to a binding partner (e.g., receptor "binding sites"). For example, in one embodiment, screening assays may be carried out using polypeptides (or fusions thereof) that comprise an amino acid sequence corresponding to a mature, full length Eta-1 polypeptide (e.g., comprising the sequence of amino acid residues 1–299 of the Eta-1 polypeptide set forth in FIG. 2 and in SEQ ID NO: 2). In another embodiment, screening assays may be carried out using a truncated Eta-1 polypeptide which, preferably, retains the biological activity of a full length Eta-1 chemokine.

A variety of methods are known in the art that may be used to identify specific binding sites of an Eta-1 polypeptide. For example, binding sites may be identified by mutating an Eta-1 gene and screening for disruptions of binding as described above. A gene encoding the binding partner may also be mutated in such assays to identify mutations that compensate for disruptions from the mutation to the Eta-1 gene. Sequence analysis of these mutations can then reveal mutations that correspond to the binding region of the two proteins.

In an alternative embodiment, a protein (e.g., an Eta-1 protein or a protein binding partner to an Eta-1 protein) may be anchored to a solid surface or support using the methods described herein above. Another labeled protein which binds to the protein anchored to the solid surface may be treated with a proteolytic enzyme, and its fragments may be allowed to interact with the protein attached to the solid surface, according to the methods of the binding assays described supra. After washing, short, labeled peptide fragments of the treated protein may remain associated with the anchored protein. These peptides can be isolated and the region of the full length protein from which they are derived may be identified by the amino acid sequence.

In still other embodiments, compounds that interfere with an Eta-1 receptor interaction may also be identified by screening for compounds that modulate binding of an Eta-1 polypeptide (for example, an Eta-1-Fc fusion polypeptide) to cells that express an Eta-1 specific receptor.

Therapeutic Methods and Pharmaceutical Preparations

The Eta-1 nucleic acid molecules, polypeptides and antibodies of the present invention may also be used in therapeutic methods and compositions, e.g., to modulate or enhance an immune response. In particular, without being bound by any particular theory, Eta-1 of the present invention is believed to enhance or stimulate an immune response by activating dendritic cells and natural killer cells and activation and proliferation of T-lymphocytes (CD4+ and CD8+), and induction of Th1 cytokines, predictably, by drawing such cells to a site where the Eta-1 is introduced or released. Accordingly, the introduction of Eta-1 to a site of infection may draw mobile cells (e.g., leukocytes) to that site and thereby augment an immune response to the infection. For example, the deliberate introduction of Eta-1 to a vaccination site draws mobile cells to that site and augments an immune response to the vaccine antigen or antigens. Accordingly, in preferred embodiments, the therapeutic methods of this invention include methods for enhancing an immune response in an animal by administering an Eta-1 nucleic acid or polypeptide. In particularly preferred embodiments, the Eta-1 nucleic acids and polypeptides of the invention are administered either before, after or substantially simultaneously with an antigen or immunogen (e.g., in a vaccine) so that an immune response to the antigen or immunogen is enhanced in the animal.

In addition, the Eta-1 nucleic acids and polypeptides of the present invention are administered intratumorally or systemically by an appropriate route (i.m., s.c., i.d., i.v., i.a.) to an animal, with or without tumor disease, before, after or substantially simultaneously with an antigen or immunogen so that an immune response to the antigen or immunogen is enhanced in the animal.

Alternatively, compounds that bind to an Eta-1 nucleic acid or polypeptide of the invention, compounds that modulate expression of an Eta-1 gene, and compounds that interfere with or modulate binding of an Eta-1 nucleic acid or polypeptide with a binding compound (for example, an Eta-1 specific receptor) may also be useful, e.g., in methods for enhancing or suppressing an immune response by enhancing or suppressing Eta-1 activity.

Vaccines & Immunological Compositions & Tumor Therapy

In particularly preferred embodiments, the Eta-1 nucleic acids and polypeptides of the present invention may be used to enhance or stimulate an immune response in an animal and, in particular, to enhance or stimulate an immune response to an immunogen or tumor antigen. Accordingly, the invention provides methods and compositions for enhancing or stimulating an immune response in an animal. In preferred embodiments, the animal is a feline or canine. The invention includes Eta-1 derived from felines. In particularly preferred embodiments, feline Eta-1 of the invention may be used to enhance or stimulate an immune response in a feline.

Generally, the methods of the invention comprise administering an Eta-1 polypeptide or nucleic acid of the invention to the animal in an amount effective to enhance or stimulate an immune response to the immunogen or tumor antigen. Although, preferably the Eta-1 polypeptide or nucleic acid is administered substantially with the immunogen, the Eta-1 polypeptide or nucleic acid may, alternatively, be administered before or after the immunogen is administered. In the case of tumor therapy, Eta-1 may be administered intratumorally, systemically or by any appropriate route by itself. In such alternative embodiments, the Eta-1 nucleic acid or polypeptide is preferably administered either immediately after or prior to (e.g., within a few minutes of) administration of the immunogen. However, the Eta-1 polypeptide or nucleic acid may be administered some time (e.g., within a few days or even a few weeks) before or after administration of the immunogen. For example, in certain embodiments an immunogen may first be administered to the animal, and an Eta-1 nucleic acid or polypeptide may be administered some time later (e.g., between 1–4 weeks later) as a booster.

The immunogen may be any composition that is capable of eliciting or inducing an immune response in the animal, including but not limited to a protein, a lipoprotein, a polysaccharide or a nucleic acid. The immunogen may comprise a suspension of a live (preferably attenuated) or killed infectious agent (for example a microorganism such as a bacterium or virus, a parasite, or other pathogen) that causes an infectious disease. Alternatively, the immunogen may comprise an immunogenic polypeptide, for example a polypeptide derived from an infectious agent which may be an antigen and which therefore activates an immune response in an animal. In other embodiments, the immunogen may be a nucleic acid, such as a recombinant vector (including DNA vectors or plasmids, retroviral vectors and lentivirus vectors) that encodes an antigen and may be administered, e.g., as part of a DNA vaccine.

In a preferred embodiment, the immunogen is derived from a pathogen selected from the group consisting of viral, bacterial, rickettsial, protozoal, fungal, and parasitic pathogens, including trematodes (flukes), cestodes (tapeworms), nematodes (roundworms) and arthropods, or combinations thereof. In a preferred embodiment, the immunogen may be a viral canine pathogen such as canine herpesvirus, canine distemper virus, canine adenovirus type 1, canine adenovirus type 2, parainfluenza virus, canine parvovirus, canine coronavirus, canine herpesvirus, canine reovirus types 1, 2 and 3, or rabies virus. The immunogen may also be a bacterial canine pathogen such as *Campylobacter jejuni, Borrelia burgdorferi, Salmonella* spp., *Bordetella bronchiseptica, Brucella canis,* or *Leptospira* spp. Further, the pathogen may be a rickettsial canine pathogen such as *Neorickettsia* spp., *Ehrlichia* spp., or *Rickettsia rickettsii;* a protozoal canine pathogen, such as *Giardia* spp.; a fungal canine pathogen such as *Coccidioides immiti,* or *Histoplasma capsulatum;* or a parasitic canine pathogen such as *Toxocara* spp., and *Dirofilaria immitis.*

In another embodiment, the pathogen may be a feline pathogen of the viral type, e.g., feline immunodeficiency virus (FIV), feline syncytial virus, feline Borna disease virus, feline enteric coronavirus, rabies virus, feline viral rhinotracheitis (FVR) virus, feline calicivirus (FCV), feline panleukopenia virus, feline leukemia (FeLV) virus, feline reovirus, feline rotavirus, astrovirus, or feline sarcoma virus; of the bacterial type, e.g., *Campylobacter jejuni, Yersinia pesos,* or *Chlamydia psittaci;* of the rickettsial type, e.g., *Haemobartonedlafells*; of the protozoal type, e.g., *Toxoplasma gondii* or *Giardia lamblia;* of the fungal type, e.g., *Histoplasma capsulatum* or *Microsporum canis*; or of the parasitic type, e.g., *Toxocara* spp.

The present invention also contemplates the use of the molecules of the present to invention as cancer therapeutics, e.g., cancer vaccines. In this regard, the invention contemplates intratumoral injection of solid tumors with a DNA, viral vector, peptide, or soluble protein of the present invention, as well as systemic injection of Eta-1 (IM, SC, IV, 1P) for treatment of systemic cancer or as vaccine against cancer. Administration of Eta-1 may be by itself, or co-administered with a tumor specific antigen, or non-specific tumor antigens, such as MUC-I, HSP-70, or co-administered with cytokines such as IL-18, IL-12, and costimulatory molecules (B7.1, B7.2, CD40L).

In addition, the present invention contemplates the administration of the molecules of the invention as therapy for the treatment of autoimmune diseases and/or allergic reactions. In particular, the molecules of the invention may be used to treat osteoarthritis, rheumatoid arthritis, and skin diseases, such as psoriasis.

In still another embodiment, an Eta-1 polypeptide or nucleic acid of the present invention may be used to enhance or stimulate an immune response by expressing the Eta-1 polypeptide or nucleic acid in an infectious agent which may then be administered to an animal as a vaccine. The Eta-1 polypeptide or nucleic acid may be expressed in a microorganism, for example in a virus or bacterium, according to any of the methods described above. For example, the Eta-1 polypeptide or nucleic acid may be recombinantly expressed in a microorganism that co-expresses an antigen. Vaccines that comprise administering an infectious agent or other microorganism co-expressing an antigen and either a cytokine or chemokine have previously been described in the art and are known to effectively enhance an immune response to an infectious agent. See, for example, Gherardi et al., *J. Immunol.,* 162: 6724–6733 (1999); Kent et al., *Vaccine,* 18: 2250–2256 (2000); Narvaiza et al., *J. Immunol.,* 164: 3112–3122 (2000).

In one preferred embodiment, the antigen may also be one (e.g., a protein or protein fragment) that is recombinantly expressed in the microanimal. For example, the antigen may be from another infectious agent, which is a different type or species of infectious agent than that administered to the animal and which preferably causes or is associated with an infectious disease in the animal. In such an embodiment, the microanimal that co-expresses the antigen and Eta-1 may be used, e.g., in a vaccine, to enhance an immune response against the infectious agent which causes or is associated with the infectious disease.

In another similar embodiment, the antigen may be an antigen that is normally expressed in an infectious agent (e.g., microanimal) that is administered to an animal. For example, an Eta-1 polypeptide or nucleic acid may be expressed in a live (preferably attenuated) infectious agent that causes or is associated with an infectious disease, and the infectious agent may be administered, e.g., in a vaccine against that disease. In such an embodiment, the recombinantly expressed Eta-1 polypeptide may then function as an adjuvant, e.g., to enhance an immune response against that infectious agent or to enhance an immune response against an agent of that infectious agent.

The Eta-1 nucleic acids and polypeptides which may be administered in these methods include any of the Eta-1 polypeptides and nucleic acids of the present invention. Preferably, the Eta-1 polypeptide administered is functional (i.e., biologically active). For example, in one particular embodiment, the Eta-1 polypeptide administered comprises the amino acid sequence of the Eta-1 polypeptide set forth in FIG. 1(B) and in SEQ ID NO: 2.

Likewise, in embodiments of the invention wherein an Eta-1 nucleic acid is administered, the Eta-1 nucleic acid preferably encodes a functional Eta-1 polypeptide. For example, in one particular embodiment the Eta-1 nucleic acid administered encodes a polypeptide having the amino acid sequence of the Eta-1 polypeptide set forth in FIG. 1(B) and in SEQ ID NO: 2.

In various aspects of the invention, the Eta-1 polypeptide or nucleic acid and the immunogen may be administered as separate compositions or molecules or, alternatively, as a single molecules (e.g., a fusion or chimeric molecule). For example, in one preferred embodiment where the vaccine is a polypeptide vaccine, the methods of the invention may comprise administering a first polypeptide, which is an antigen, and a second polypeptide, which is an Eta-1 polypeptide, to the animal. Fusion polypeptides of a cytokine and an antigen are also known in the art (see, e.g., Biragyn et al., *Nature Biotechnology,* 17: 253–258 (1999)) and administration of such fusion proteins may induce a stronger immune response to an antigen than administration of either the antigen alone, or the antigen and cytokine as separate polypeptides. Thus, the methods of the invention also provide a preferred embodiment wherein a fusion protein is administered to the animal. Such fusion proteins, described supra, may comprise a polypeptide sequence for an antigen fused to an Eta-1 polypeptide sequence of the invention.

In other embodiments, the invention also provides methods for administering Eta-1 as part of a DNA vaccine. The term "DNA vaccine" is an informal term of art, and is used herein to refer to vaccines delivered by means of a recombinant vector. An alternative term used herein is "vector vaccine" (since some potential vectors, for example retroviruses and lentiviruses, are RNA viruses and since in some instances non-viral RNA instead of DNA may be delivered to cells). For example, in one preferred aspect, the methods of the invention may comprise administering a first nucleic acid molecule, which encodes an antigen, and a second nucleic acid molecule which encodes an Eta-1 polypeptide of the invention. However, the methods of the invention also include techniques that comprise administering a nucleic acid that encodes both an antigen and an Eta-1 polypeptide. For example, such methods may include ones where a single nucleic acid vector is administered which comprises coding sequences for two separate polypeptides: a first polypeptide, which is an antigen; and a second polypeptide, which is an Eta-1 polypeptide of the invention. In an alternative and particularly preferred aspect of these methods, the nucleic acid vector comprises a coding sequence for a single, fusion polypeptide of the invention. Specifically, the nucleic acid may encode a single fusion polypeptide having the sequence for an antigen fused to an Eta-1 polypeptide of the invention.

In embodiments of these methods wherein a nucleic acid is administered to the animal, the nucleic acid preferably comprises an expression vector (for example, any of the expression vectors described above) that contains nucleic acid sequences encoding either an antigen, an Eta-1 polypeptide or both. It is noted that the methods described here may also include ones where both nucleic acids and polypeptides are administered to enhance or stimulate an immune response. For example, the methods may comprise administering a polypeptide, which is an antigen, and a nucleic acid which encodes an Eta-1 polypeptide to an animal. Similarly, the methods of the invention may also comprise administering to an animal a nucleic acid which encodes an antigen, and an Eta-1 polypeptide.

Preferably, the amount of the Eta-1 nucleic acid or polypeptide administered in these methods is an amount that is sufficient to elicit, enhance or stimulate an immune response to the immunogen. A variety of methods are known in the art to determine whether an immune response has been enhanced. Alternatively, lymphocytes may also be tested for T cell mediated responses, e.g., by measuring their proliferative or target cell killing responses to the immunogen in vitro. Such measurements are preferably made in animals vaccinated according to the above-described methods and compared to similar measurements in an animal vaccinated with the immunogen alone. An increase in either the level of antibodies to the immunogen, T cell proliferative responses to the immunogen, or both may be indicative of an enhanced or stimulated immune response to the immunogen.

A vaccine or tumor therapeutic regimen generally comprises a therapeutically effective dose of an immunogen (e.g., an antigen of an infectious agent, tumor antigen, fixed tumor cells) and, preferably, an adjuvant and/or a pharmaceutically acceptable carrier. The term "adjuvant" refers to a compound or mixture that enhances the immune response to an antigen. An adjuvant can serve, e.g., as a tissue depot that slowly releases the antigen, and also as a lymphoid system activator that enhances the immune response (see Hood et al., *Immunology,* Second Ed., 1984, Benjamin/Cummings: Menlo Park, Calif., p. 384). Exemplary adjuvants include, but are not limited to, Freund's adjuvant (complete and incomplete), saponin, mineral gels such as aluminum hydroxide, surface active substances (for example, lysolecithin), pluronic polyols, polyanions, peptides, oil or hydrocarbon emulsions, keyhole limpet hemocyanins, dinitrophenol, and potentially useful human adjuvants such as BCG (*bacille Calmette-Guerin*) and *Corynebacterium parvum*. Immunostimulating complexes, or "iscoms," such as those described in U.S. Pat. No. 5,178,860, may also be used as adjuvants. In addition, immunostimulatory proteins, such as chemokines, may be provided as an adjuvant to increase the immune response to a vaccine. The choice of an adjuvant will depend in part on the stability of the vaccine in the presence of the adjuvant, the route of administration, and the regulatory acceptability of the adjuvant.

Generally, the amount of an Eta-1 nucleic acid or polypeptide that is an effective amount for enhancing or stimulating an immune response will depend, inter alia, on the route of administration and will vary according to the species to be protected and on the total weight of the animal. Thus, for example, in embodiments wherein the vaccine is a polypeptide vaccine, exemplary effective amounts of a peptide or polypeptide antigen will range from 1–1000 µg. Similarly, exemplary effective amounts of an Eta-1 polypeptide administered as an adjuvant in vaccines or a therapeutic regimen may be between about 1 and 100 µg. In other embodiments, wherein the vaccine is a DNA vaccine, exemplary effective amounts of a nucleic acid (e.g., a plasmid) encoding an antigen will be from about 0.1 and 500 µg, and exemplary effective amounts of a nucleic acid (e.g., a plasmid) encoding an Eta-1 polypeptide will be from about 0.1 and 500 µg. One or more additional administrations may be provided as booster doses at appropriate intervals.

Both the immunogen and the Eta-1 nucleic acids or polypeptides may be administered as vaccines or immunological compositions to an animal by, e.g., inhalation, immersion or insufflation (either through the mouth or through the nose), or by oral, bucal, rectal or parenteral administration (e.g., by subcutaneous, intramuscular, intraorbital, intracapsular, intraspinal, intrasternal or intravenous injection and the like). A vaccine may also be administered by particle-mediated transfer (e.g., using a "particle gun"). Particle transfer methods of administration are particularly preferred for DNA vaccines. See, for example, Gainer et al., *J Neurooncol.,* 47: 23–30 (2000); Koide et al., *Jpn J. Pharmacol,* 83: 167–174 (2000);

Kuriyama et al., *Gene Ther.*, 7: 1132–1136 (2000); and Yamauchi et al., *J. Exp. Zool.*, 287: 285–293 (2000). A tumor therapeutic composition may be administered directly into tumors (intratumorally) or systemically through the routes described above.

Other immunization strategies include encapsulating the immunogen and Eta-1 in microcapsules (U.S. Pat. Nos. 5,075,109, 5,820,883 and 5,853,763) or using an immunopotentiating membranous carrier. Immunogenicity of orally administered immunogens may be further enhanced by using, e.g., red blood cells (IRBC) or RBC ghosts or blue tongue antigen.

The invention also contemplates use of Eta-1 nucleic acids and/or polypeptides to stimulate or enhance an immune response in a passive immunization strategy. Passive immunization methods are ones that comprise administering, instead of or in addition to an immunogen, an antibody that is reactive with, and is preferably generated against, the immunogen. Passive immunization strategies are particularly effective for an incipient or established infection before the host's immune system can respond. Thus, the methods of the invention also include ones for enhancing or stimulating an immune response to an immunogen by administering an antibody reactive with (preferably generated against) the immunogen, and an Eta-1 polypeptide or nucleic acid of the invention.

Antibodies for use in a passive immunization therapy may be obtained, e.g., from the serum of affected animals which are preferably of the same species as the infected host. Thus, for example, antibodies from blood serum of an animal can be isolated, preferably by affinity purification against an epitope of the immunogen, and used to passively immunize newly infected animals of the same species. Alternatively, antibodies may be generated against the immunogen or an antigen derived therefrom. Thus, the above-described vaccination strategy may also be used to generate antibodies for passive immunization.

The invention also provides pharmaceutical compositions that may be used as vaccines in the above-described methods to enhance or stimulate an immune response to an immunogen. These pharmaceutical compositions comprise an Eta-1 polypeptide or an Eta-1 nucleic acid of the present invention in an amount effective to stimulate an immune response in combination with one or more pharmaceutically acceptable carriers. Sterile water or aqueous saline, dextrose, and/or glycerol solutions optionally may be employed as carriers particularly for injectable preparations. In preferred embodiments, the pharmaceutical compositions further comprise an immunogen. For example, the pharmaceutical compositions may also comprise an immunogenic polypeptide (i.e., an antigen), or they may comprise a nucleic acid (e.g., a nucleic acid vector or plasmid) that encodes an immunogenic polypeptide. Pharmaceutical compositions of the invention are further discussed below (see "Pharmaceutical Preparations", infra).

Inhibitory Approaches

In alternative embodiments, the present invention provides methods and compositions for modulating (e.g., enhancing or suppressing) an immune response by modulating (e.g., increasing or decreasing) the expression or activity of an Eta-1 gene or its gene product. Such methods may simply comprise administering one or more compounds that modulate expression of an Eta-1 gene, synthesis of an Eta-1 gene product or Eta-1 gene product activity so the immune response is modulated (e.g., enhanced or suppressed). Preferably, these one or more compounds are administered until the immune response is modulated as desired.

Among the compounds that may exhibit an ability to modulate the activity, expression or synthesis of an Eta-1 nucleic acid are antisense, ribozyme and triple-helix molecules. Such molecules may be designed to reduce or inhibit wild-type Eta-1 nucleic acids and polypeptides or, alternatively, may target mutant Eta-1 nucleic acids or polypeptides.

Antisense RNA and DNA molecules act to directly block the translation of mRNA by hybridizing to target mRNA molecules and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

In one preferred embodiment, oligonucleotides complementary to non-coding regions of an Eta-1 gene may be used in an antisense approach to inhibit translation of endogenous Eta-1 mRNA molecules. Antisense nucleic acids are preferably at least six nucleotides in length, and more preferably range from between about six to about 50 nucleotides in length. In specific embodiments, the oligonucleotides may be at least 10, at least 15, at least 20, at least 25 or at least 50 nucleotides in length.

It is generally preferred that in vitro studies are first performed to quantitate the ability of an antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

While antisense nucleotides complementary to the target gene coding region sequence could be used, those complementary to the transcribed, untranslated region are most preferred.

Antisense molecules are preferably delivered to cells, such as hematopoictic cells, that express the target gene in vivo. A number of methods have been developed for delivering antisense DNA or RNA to cells. For example, antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

Preferred embodiments achieve intracellular concentrations of antisense nucleic acid molecules which are sufficient to suppress translation of endogenous mRNAs. For example, one preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector, as set forth above, can be introduced such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in the particular cell type (for example in a hemopoietic cell). For example, any of the promoters discussed supra in connection with the expression of recombinant Eta-1 nucleic acids can also be used to express an Eta-1 antisense nucleic acid.

Ribozyme molecules designed to catalytically cleave target gene mRNA transcripts can also be used to prevent translation of target gene mRNA and, therefore, expression of target gene product (see, e.g., International Publication No. WO 90/11364; Sarver, et al., *Science,* 247: 1222–1225 (1990)).

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in, e.g., Myers, 1995, *Molecular Biology and Biotechnology: A Comprehensive Desk Reference,* VCH Publishers, New York, 1995 (see especially FIG. 4, page 833).

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., *Science,* 224: 574–578 (1984); Zaug and Cech, *Science,* 231: 470–475 (1986); Zaug et al., *Nature,* 324: 429–433 (1986); International Patent Publication No. WO 88/04300; Been and Cech, *Cell,* 47: 207–216 (1986)). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter so that transfected cells will produce sufficient quantities of the ribozyme to destroy endogenous target gene messages and inhibit translation. Because ribozymes, unlike antisense molecules, are catalytic, a lower intracellular concentration is required for efficacy. Such constructs can be introduced to cells using any of the vectors described supra.

Endogenous target gene expression can also be reduced by inactivating or "knocking out" the target gene or its promoter using targeted homologous recombination. For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited where modifications to embryonic stem cells can be used to generate animal offspring with an inactive target gene. But this approach can be adapted for use in other species of animal (for example, in felines) provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body (see generally, Helene, *Anticancer Drug Des.,* 6: 569–584 (1991); and Maher, *Bioassays,* 14: 807–815 (1992)).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, that contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may be introduced into cells via gene therapy methods such as those described herein, that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Pharmaceutical Preparations

Compounds that are determined to affect Eta-1 gene expression or Eta-1 gene product activity may be administered at therapeutically effective doses to modulate an immune response (e.g., antibody levels or proliferative and cytotoxic T cell activity). Alternatively, and in preferred embodiments, Eta-1 nucleic acids and/or polypeptides of the invention may also be administered, preferably in combination with an immunogen, in an amount effective to enhance or stimulate an immune response in the animal. Thus, the invention also provides pharmaceutical preparations for use, e.g., as vaccines or as therapeutic compounds, to modulate, stimulate or enhance an immune response in an animal. The terms "therapeutically effective dose" and "effective amount" refer to the amount of the compound that is sufficient to result in such a modulated, enhanced or stimulated immune responses.

Toxicity and therapeutic efficacy of compounds can be determined by standard pharmaceutical procedures, for example in cell culture assays or using experimental animals to determine the $LD_{50}$ and the $ED_{50}$. The parameters $LD_{50}$ and $ED_{50}$ are well known in the art, and refer to the doses of a compound that are lethal to 50% of a population and therapeutically effective in 50% of a population, respectively. The dose ratio between toxic and therapeutic effects is referred to as the therapeutic index and may be expressed as the ratio: $LD_{50}/ED_{50}$. It is particularly preferable to use delivery systems that specifically target such compounds to the site of affected tissue so as to minimize potential damage to other cells, tissues or organs and to reduce side effects.

Data obtained from cell culture assay or animal studies may be used to formulate a range of dosages for use in an animal. The dosage of compounds used in therapeutic methods of the present invention preferably lie within a range of circulating concentrations that includes the $ED_{50}$ concentration but with little or no toxicity (e.g., below the $LD_{50}$ concentration). The particular dosage used in any application may vary within this range, depending upon factors such as the particular dosage form employed, the route of administration utilized, the conditions of the individual (e.g., patient), and so forth.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms (e.g., as determined from the cell culture assays). Appropriate dosages for use in a particular individual, for example in human patients, may then be more accurately determined using such information.

Pharmaceutical compositions for use in accordance with the present invention may be formulated in a conventional manner using one or more physiologically acceptable carriers. As used herein, the term "carrier" refers to a diluent, adjuvant, excipient or vehicle with which a compound is administered. Exemplary suitable pharmaceutical carriers are described in "Remington's Pharmaceutical Sciences", $18^{th}$ ed., A. Gennaro (ed.), Mack Publishing Co., Easton, Pa.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients, such as binding agents (e.g., pregelatinised maize starch, polyvinylpyrrolidone or hydroxypropyl methylcellulose), fillers (e.g., lactose, microcrystalline cellulose or calcium hydrogen phosphate), lubricants (e.g., magnesium stearate, talc or silica), disintegrants (e.g., potato starch or sodium starch glycolate), or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration, the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may, for example, comprise metal or plastic foil, such as a blister pack. The pack or dispenser device may be accompanied by instructions for administration.

EXAMPLES

The present invention is also described by means of particular examples. However, the use of such examples anywhere in the specification is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

Cloning of Feline Eta-1

Feline peripheral blood mononuclear cells (PBMC) were extracted from cats and cultured with Concanavalin A for 16 hours at 37° C. Cells were pelleted, washed with PBS, and used to isolate total RNA (Qiagen RNeasy Total RNA System, Santa Clara, Calif.). Total RNA was treated with DNAse I (Boehringer Mannheim, Indianapolis, Ind.) to remove DNA contamination from the RNA preparations. Messenger RNA (mRNA) was then extracted from these preparations, using Qiagen's Oligotex beads (Santa Clara, Calif.) and quick columns. Copy DNA (cDNA) was generated from mRNA, in the presence of random hexamers, dNTPs, RNAsin, reverse transcriptase (Promega, Madison, Wis.), and reverse transcriptase buffer (Promega, Madison, Wis.) and incubated at 42° C. for 30 minutes. For cloning feline Eta-1, PCR was then used to generate a double stranded, cDNA clone of the feline open reading frame (ORF) using degenerate primers designed from the 5' and 3' ends of human and mouse Eta-1 sequences. The sense primer, 5'-ACCATGAGATTGGCAGT-GATTTGCTTTTGCCT-3' (SEQ ID NO: 5) and antisense primer 5'-TTAATTGACCTCAGAAGATGCAC-TATCTAATTCATGAG-3' (SEQ ID NO: 6) were combined with dNTPs, cDNA (1$^{st}$ strand), MgSO$_4$, Vent polymerase (BRL, Bethesda, Md.) and Vent polymerase buffer (BRL, Bethesda, Md.), and PCR was performed.

PCR conditions were as follows: 1 cycle of 94° C. for 15 seconds, 35 cycles of 94° C. for 30 seconds, 55° C. for 2 minutes, 72° C. for 2 minutes and 1 cycle of 72° C. for 10 minutes. PCR reactions were run on a 1% low melt agarose gel and DNA fragments corresponding to the expected size of the Eta-1 ORF were isolated, gel purified (Qiagen's Gel Purification Kit, Santa Clara, Calif.) and cloned into a pCR-BLUNT plasmid vector using kit reagents from Invitrogen's Zero Blunt PCR Cloning Kit, including M13 sequences 5' and 3' of multiple cloning site (San Diego, Calif.). DNA extracted from kanamycin resistant bacterial colonies was sequenced using ABI's fluorescenated automated sequencing protocols and equipment (Perkin-Elmer-Cetus, Boston, Mass.; Applied Biosystems, Inc., Foster City, Calif.). Feline Eta-1 was sequenced using M13 forward and reverse primers (Invitrogen, San Diego, Calif.). Two resultant Eta-1 clones were designated 1111-42.3 and 1111-42.6.

To facilitate the cloning of the feline Eta-1 gene behind any pox promoter containing EcoRI and BamHI cloning sites, two new primers were designed to introduce EcoRI and BamHI restriction enzymes cloning sites onto the 5' and 3' end of the Eta-1 ORF, respectively. These two primers were: sense primer 5'-GACTGAATTCATGAGATTG-GCAGTG-3' (SEQ ID NO: 7) and antisense primer Eta-1 5'-GGTAGGATCCTTAATTGACCTCAG-3' (SEQ ID NO: 8). The resultant PCR fragment was digested with EcoRI and BamHI, and cloned into a HindIII K SPV homology vector (EcoRI insertion site within the swinepox virus HindIII K genomic fragment) for the generation of a recombinant SPV virus. This resulted in the cassette, a SPV HindIII K homology vector containing the feline Eta-1 ORF behind the late/early synthetic pox promoter, and adjacent to the E. coli uidA marker gene cassette promoted by synthetic late pox promoter, LP2. Plasmid vector was co-transfected with SPV-001 (wild-type) to generate a recombinant SPV virus expressing the feline Eta-1 and E. coli β-glucuronidase proteins.

Example 2

Characterization of the Feline Eta-1 cDNA and Polypeptide

The isolated and purified feline Eta-1 cDNA of approximately 897 nucleotides that code for an open reading frame of the feline Eta-1 polypeptide of approximately 299 amino acids was cloned into a swinepox expression vector. Feline Eta-1 protein was detected in the supernatants of ESK-4 cells infected with the SPV/Eta-1 viral vector at 24, 48 and 72 hours post infection by Western blot analysis using anti-human Eta-1 polyclonal antibody. The anti-human Eta-1 antibody reacted with a single protein band at approximately 50 kDa. The feline Eta-1 sequence predicts a secreted and posttranslationally processed protein, a molecular mass of about 50–60 kDa after post translational processing, an isoelectric point of about 4.428, and a net charge at pH 7.0 of −30.093. The sequence predicts a very hydrophilic, secreted protein (no hydrophobic transmembrane region), with two N-linked glycosylation sites, an RGD cell adhesion peptide, with a signal peptide sequence of approximately 18 amino acids at the N-terminus. Feline Eta-1 is also predicted to be phosphorylated.

Example 3

A recombinant swinepox virus containing feline Eta-1 driven by the synthetic pox promoter, LP2EP2, was constructed by the method of homologous recombination. Briefly, ESK-4 cells were infected with SPV-001 (wild-type SPV) at a MOI of 0.01 for 4–6 hours at 37° C., followed by transfection with 15 μg of SPV K homology vector containing feline Eta-1, using lipofectin reagent (Gibco/BRL, Bethesda, Md.). Infected/transfected ESK-4 cells were allowed to reach complete CPE. Lysates were harvested and screened for recombinant plaques expressing E. coli β-glucuronidase as previously described (Winslow et al., 2002, publication in prep).

Recombinant plaques were grown in ESK-4 cells to produce high-titered viral stocks. Purity of recombinant viral stocks was confirmed by black plaque analysis staining with anti-β-glucuronidase antibody. Expression of feline Eta-1 was confirmed by Western blot analysis using goat anti-human Eta-1, as shown in FIG. 5. The resultant SPV/Eta-1 virus was designated SPV-383.

Example 4

Cloning of a Partial Internal Sequence of Canine Eta-1

Spleen cells were extracted from dogs and cultured with Concanavalin A for 16 hours at 37° C. Cells were pelleted, washed with PBS, and used to isolate total RNA (Qiagen RNeasy Total RNA System, Santa Clara, Calif.). Total RNA was treated with DNAseI (Boehringer Mannheim, Indianapolis, Ind.) to remove DNA contamination from the RNA preparations. Messenger RNA was then extracted from these preparations, using Qiagen's Oligotex beads (Santa Clara, Calif.) and quick columns. Copy DNA was generated from mRNA, in the presence of random hexamers, dNTPs, RNAsin, reverse transcriptase (Promega, Madison, Wis.) and reverse transcriptase buffer (Promega, Madison, Wis.) and incubated at 42° C. for 30 minutes. PCR was then used to generate a double stranded, partial cDNA sequence representing approximately one-third of the predicted full-length sequence. The sense primer 5'-CCTGACCCATCTCAGAAGCAGAATCTCCTWGCSCCACAG-3' (SEQ ID NO: 9) and antisense primer 5'-GACCTCAGTCCATAARCCAMRCTATCACCTCGGCC-3' (SEQ ID NO: 10), were incubated with dNTPs, cDNA ($1^{st}$ strand), $MgSO_4$, Vent polymerase (BRL, Bethesda, Md.) and Vent polymerase buffer (BRL, Bethesda, Md.), and PCR was performed.

PCR conditions were as follows: 1 cycle of 94° C. for 15 seconds, 35 cycles of 94° C. for 30 seconds, 55° C. for 2 minutes, 72° C. for 2 minutes and 1 cycle of 72° C. for 10 minutes. PCR reactions were run on a 1% low melt agarose gel and DNA fragments corresponding to the expected size of the partial Eta-1 ORF fragment (326 bp) were isolated, gel purified (Qiagen's Gel Purification Kit, Santa Clara, Calif.) and cloned into a pCR-BLUNT plasmid vector using kit reagents from Invitrogen's Zero Blunt PCR Cloning Kit, including M13 sequences 5' and 3' of multiple cloning site (San Diego, Calif.). DNA extracted from kanamycin resistant bacterial colonies was sequenced using ABI's fluorescenated automated sequencing protocols and equipment (Perkin-Elmer-Cetus, Boston, Mass.; Applied Biosystems, Inc., Foster City, Calif.) and using M13 forward and reverse primers (Invitrogen, San Diego, Calif.). The resultant Eta-1 clone consisted of 320 bp (106 amino acids) of canine Eta-1 sequence predicted to be approximately ⅓ of the full-length canine Eta-1 sequence, as shown in SEQ ID NO: 3 and SEQ ID NO: 4. This sequence also contained the predicted two N-linked glycoyslation sites and an RGD sequence. The resultant partial canine Eta-1 clone was designated 1116-36.55.

Example 5

Cloning of Full-Length Canine Eta-1

Eta-1 cDNA is cloned by first RT-PCR (Reverse transcriptase/Polymerase chain reaction) amplifying a region between two sequences that are conserved enough to make degenerate primers that interact with these canine mRNA (Example 4). The source of the mRNA is canine splenocytes stimulated for at least 16 hours with ConA. The partial canine cDNA PCR product is sequenced (SEQ ID NO: 3). The sequence is used to make primers for RACE (rapid amplification of cDNA ends) PCR. The 5' end is amplified by first making cDNA with a downstream primer complimentary to the newly sequenced conserved region. An oligonucleotide is ligated to the 3' end of the cDNA (compliment with the 5' end of mRNA). This sequence serves as the binding site for the upstream primer, which is PCR compatible with the downstream PCR primer that corresponds with another region in the newly sequenced region. Degenerate primers are employed in multiple rounds of nested reactions to obtain the 3' end. This upstream primer for PCR is designed to react with a sequence in the newly sequenced region. Products are either sequenced directly or cloned into a TA cloning vector and sequenced from the plasmid. The whole open reading frame is cloned by amplifying in its entirety by PCR with primers constructed from the known sequences. The ORFs are cloned and sequenced three times.

Example 6

Feline Eta-1 Mammalian Expression Plasmid

To generate a vector for the purpose of DNA vaccination, a mammalian expression plasmid containing feline or canine Eta-1 driven by the cytomegalovirus (CMV) immediate early promoter was constructed by standard cloning methods. The resultant feline Eta-1 expression vector was designated 1102-76.5. DNA plasmids (5–15 μg/6 cm dish) were transfected into a mammalian cell line, such as CRFK or MDBK, using lipofectin or calcium phosphate reagent. Supernatant was collected after 48 hours and tested for the presence of secreted Eta-1 protein by Western blot analysis using anti-human Eta-1.

Example 7

Use of Feline Eta-1 Polypeptide in Vaccines

The following experiments are performed to evaluate the immune-enhancing activities of feline Eta-1 in feline vaccines. Cats at 8–12 weeks of age are injected intramuscularly, subcutaneously or intranasally with 100 μg of plasmid containing cDNA for feline Eta-1 molecules in a mixture with a plasmid containing cDNA for FIV env and gag, or FeLV env and gag, or FIP nucleocapsid. Controls cats do not receive Eta-1. Cats are challenged with virulent FeLV, FIV or FIP and observed for signs of disease, as described above. The results of the challenge experiment are that cats receiving the cDNA vector containing feline Eta-1 vector containing FIV genes, FeLV genes, or FIP genes show 75–100% protection from disease compared to cats receiving only cDNA vector containing FIV genes, FeLV, or FIP genes who show 80% infection or clinical signs of disease.

In an alternate procedure, cats at 8–12 weeks of age are injected intramuscularly, subcutaneously or intranasally with 0.1 to 100 mg of purified protein for feline Eta-1 molecules from recombinant cDNA vectors described above, and injected intramuscularly with 0.1 to 100 mg of a subunit vaccine containing FIV env and gag, or FeLV env and gag, or FIP nucleocapsid. Control cats do not receive Eta-1. Cats are challenged with a virulent FIV strain, FeLV strain or FIP strain and observed regularly for development of disease. The results of the challenge experiment are that cats receiving the purified protein for feline Eta-1 and subunit vaccine containing FIV or FeLV show significantly reduced incidence of disease compared to cats receiving only subunit vaccine containing FIV or FeLV proteins.

Example 8

Cats at 8–12 weeks of age are injected intramuscularly, subcutaneously or intranasally with 5.0–8.0 log $TCID_{50}$/cat of a poxvirus, herpesvirus or adenovirus vector containing cDNA for feline Eta-1 molecules in a mixture of viruses containing cDNA for FIV env and gag, or FeLV env and gag, or FIP nucleocapsid, or coexpressed in the same viral vector containing cDNA for FIV env and gag, or FeLV env and gag, or FIP nucleocapsid. Controls cats do not receive Eta-1. Cats are challenged with virulent FeLV, FIV or FIP and observed for signs of disease, as described above. The results of the challenge experiment are that cats receiving the vector(s) containing feline Eta-1 and FIV genes, FeLV genes or FIP genes show 75–100% protection from disease compared to cats receiving only cDNA vector containing FIV genes, FeLV or FIP genes who show 80% infection or clinical signs of disease.

Example 9

Intratumoral Injection With DNA or Viral Vector Containing Eta-1 or Subunit Eta Protein Dogs and/or cats of all ages (>10 weeks of age) afflicted with tumors amenable to intratumoral injection are treated with plasmid DNA containing Eta-1 DNA (1–500 μg/treatment), viral vectors containing Eta-($1\times10^6$–$1\times10^9$ pfu/treatment) or with Eta-1 subunit protein (0.1 μg–1 mg/treatment). Injection is located intra- and peri-tumoral. DNA plasmids or viral vectors containing Eta-1 or subunit protein is either given alone or in combination. DNA plasmids or viral vectors containing Eta-1 are also coexpressed with tumor associated antigens, cytokines or other immunological immune molecules and administered alone or in combination. If needed, repeat treatments are given no more than once every week (depending on patient availability) for up to 8 weeks, depending on the response of the tumor and condition of the patient. Animals/tumors are monitored for tumor reduction, reduction in overall disease, survival time, volume of tumor, volume of metastatic disease and quality of life. Outcome is based on historical data generated from dogs and cats not treated for cancer disease, or dogs and cats treated with conventional therapies, such as chemotherapy and radiation.

Example 10

Vaccination against Cancer

Dogs and/or cats of all ages (>10 weeks of age) were treated with plasmid DNA containing Eta-1 (1–500 μg/treatment), viral vectors (poxvirus, adenovirus, herpesvirus) containing Eta-1 ($1\times10^6$–$1\times10^9$ pfu/treatment) or with Eta-1 subunit protein (0.1 μg–1 mg/treatment) in combination with tumor specific antigens, such as CEA, MAGE 1, gp100, and/or cytokines, such as IL-18, IL-12 or B7 costimulatory molecules, presented in DNA, or viral vectors. Route of administration is subcutaneous, intramuscular, intranasal or intravenous. Animals are monitored over their life span for the absence of cancer and compared to untreated animals Example 11

Systemic Administration for Treatment of Lymphoma and Leukemia

Dogs and/or cats of all ages (>10 weeks of age) diagnosed with lymphoproliferative diseases are treated with plasmid DNA containing Eta-1 (1–500 μg/treatment), viral vectors (poxvirus, adenovirus, herpesvirus) containing Eta-1 ($1\times10^6$–$1\times10^9$ pfu/treatment) or with Eta-1 subunit protein (0.1 μg–1 mg/treatment) alone or in combination with cytokines, such as IL-18, IL-12 or B7 costinulatory molecules, also presented in DNA, or viral vectors, at similar doses, as described above. Repeat treatments are given no more than once every week (depending on patient availability) for up to 8 weeks, depending on the response of the disease and condition of the patient. Animals/tumors are monitored for reduction in lymphoproliferative disease, survival time, volume of metastatic disease, toxicity and quality of life. Outcome is based on historical data generated from dogs and cats afflicted with lymphoproliferative disease, not treated for disease, or treated with conventional therapies, such as chemotherapy and radiation.

Example 12

Treatment of Osteoarthritis and Rheumatoid Arthritis

Dogs and/or cats of all ages (>10 weeks of age) afflicted with arthritic disease are treated with plasmid DNA containing Eta-1 (1–500 μg/treatment), viral vectors containing Eta-1 ($1\times10^6$–$1\times10^9$ pfu/treatment) or with Eta-1 subunit protein (0.1 μg–1 mg/treatment). Route of administration is subcutaneous, intramuscular, intranasal, intraperitoneal, or intravenous. DNA plasmids or viral vectors containing Eta-1 or subunit protein is either given alone or in combination, or in combination with other immunosuppressive therapy. If needed, repeat treatments are given no more than once every week (depending on patient availability) for up to 8 weeks, depending on the response of the disease and condition of the patient. Animal/tumors are monitored for reduction in overall disease, survival time, toxicity and quality of life. Outcome is based on historical data generated from dogs and cats not treated for arthritic disease or treated with conventional therapy.

The present invention is not to be limited in scope by the specific embodiments described herein. Indeed, various modifications of the invention, in addition to those described herein, will become apparent to those skilled in the art from the foregoing description and the accompanying figures. Such modifications are intended to fall within the scope of the appended claims.

All patents, applications, publications, test methods, literature, and other materials cited herein are hereby incorporated by reference in their entirety.

We claim:

1. An isolated or recombinant nucleic acid encoding a polypeptide comprising the amino acid sequence of SEQ ID NO: 2.

2. The nucleic acid of claim 1, which is an RNA.

3. A recombinant vector comprising the nucleic acid of claim 1.

4. The recombinant vector of claim 3, wherein the nucleic acid is operatively linked to a regulatory element.

5. An isolated host cell comprising the vector of claim 3.

6. An isolated or recombinant nucleic acid encoding a polypeptide comprising the amino acid sequence of SEQ ID NO: 4.

7. The nucleic acid of claim 6, which is an RNA.

8. A recombinant vector comprising the nucleic acid of claim 6.

9. The recombinant vector of claim 8, wherein the nucleic acid is operatively linked to a regulatory element.

10. An isolated host cell comprising the vector of claim 9.

11. The nucleic acid of claim 1 comprising the nucleotide sequence of SEQ ID NO: 1.

12. The nucleic acid of claim 6 comprising the nucleotide sequence of SEQ ID NO: 3.

13. The nucleic acid of claim 11, which is an RNA.

14. A recombinant vector comprising the nucleic acid of claim 11.

15. The recombinant vector of claim 14, wherein the nucleic acid is operatively linked to a regulatory element.

16. An isolated host cell comprising the vector of claim 14.

17. The nucleic acid of claim 12, which is an RNA.

18. A recombinant vector comprising the nucleic acid of claim 12.

19. The recombinant vector of claim 18, wherein the nucleic acid is operatively linked to a regulatory element.

20. An isolated host cell comprising the vector of claim 18.

* * * * *